United States Patent
Bauer et al.

(10) Patent No.: US 9,655,979 B2
(45) Date of Patent: May 23, 2017

(54) RNA TRANS-SPLICING MOLECULE (RTM) FOR USE IN THE TREATMENT OF CANCER

(71) Applicant: Johann Bauer, Salzburg (AT)

(72) Inventors: Johann Bauer, Salzburg (AT);
Christina Gruber, Bad Vigaun (AT);
Ulrich Koller, Neumarkt am Wallersee (AT)

(73) Assignees: Johann Bauer, Salzburg (AT);
Christina Gruber, Bad Vigaun (AT);
Ulrich Koller, Neumarkt am Wallersee (AT)

( * ) Notice: Subject to any disclaimer, the term of this patent is extended or adjusted under 35 U.S.C. 154(b) by 0 days.

(21) Appl. No.: 14/438,625

(22) PCT Filed: Oct. 31, 2013

(86) PCT No.: PCT/EP2013/072823
§ 371 (c)(1),
(2) Date: Apr. 26, 2015

(87) PCT Pub. No.: WO2014/068063
PCT Pub. Date: May 8, 2014

(65) Prior Publication Data
US 2015/0250901 A1    Sep. 10, 2015

(30) Foreign Application Priority Data
Nov. 2, 2012  (GB) .................................. 1219762.0

(51) Int. Cl.
*A61K 48/00* (2006.01)
*C12N 15/11* (2006.01)
*C12N 15/113* (2010.01)
*C12N 9/12* (2006.01)

(52) U.S. Cl.
CPC .......... *A61K 48/0058* (2013.01); *A61K 48/00* (2013.01); *C12N 9/1211* (2013.01); *C12N 15/111* (2013.01); *C12N 15/113* (2013.01); *C12N 15/1138* (2013.01); *C12N 2310/11* (2013.01); *C12N 2310/3519* (2013.01); *C12N 2320/33* (2013.01)

(58) Field of Classification Search
USPC ........... 435/6.11, 6.12, 91.1, 91.31, 455, 6.1, 435/320.1, 325; 514/44; 536/23.1, 23.2, 536/24.5
See application file for complete search history.

(56) References Cited

FOREIGN PATENT DOCUMENTS

WO    WO 2004/006678 A1    1/2004
WO    WO 2010/012472 A1    2/2010

OTHER PUBLICATIONS

Wally et al, J. of Investigative Dermatol., vol. 132, pp. 1959-1966 (2011).*
Gruber et al, Molec. Cancer Therap., vol. 10, No. 2, pp. 233-241 (2011).*
Gruber, Christina et al., "Spliceosome-Mediated RNA Trans-Splicing Facilitates Targeted Delivery of Suicide Genes to Cancer Cells," *Molecular Cancer Therapeutics*, 2011, 10(2):233-241.
Gruber, Christina et al., "The design and optimization of RNA trans-splicing molecules for skin cancer therapy," *Molecular Oncology*, 2013, 7(6):1056-1068.
Wally, Verena et al., "Spliceosome-Mediated Trans-Splicing: The Therapeutic Cut and Paste," *The Journal of Investigative Dermatology*, 2012, 132(8):1959-1966.

* cited by examiner

*Primary Examiner* — Jane Zara
(74) *Attorney, Agent, or Firm* — Saliwanchik, Lloyd & Eisenschenk

(57) ABSTRACT

The present invention pertains to a novel pre-mRNA trans-splicing molecule (RTM) comprising a binding region which is complementary to a pre mRNA of a tumor associated gene, and a coding domain which encodes for a suicide gene. Specific embodiments of the present invention relate to RTMs which mediate trans-splicing of a suicide gene, such as thymidine kinase from herpes simplex virus (HSV-tk), with the pre mRNA of the squamous cell carcinoma associated gene solute carrier organic anion transporter family member 1B3 (SLCO1B3). The invention provides RTMs which selectively kill cells expressing SLCO1B3 and which are thus useful in the treatment of cancer, specifically squamous cell carcinoma associated with epidermolysis bullosa. Also provided are methods, kits and pharmaceutical compositions relating to the RTMs in accordance to the invention.

3 Claims, 11 Drawing Sheets

FIG. 1B

RNA TRANS-SPLICING MOLECULE (RTM) FOR USE IN THE TREATMENT OF CANCER

CROSS REFERENCE TO A RELATED APPLICATION

Figure 1A:
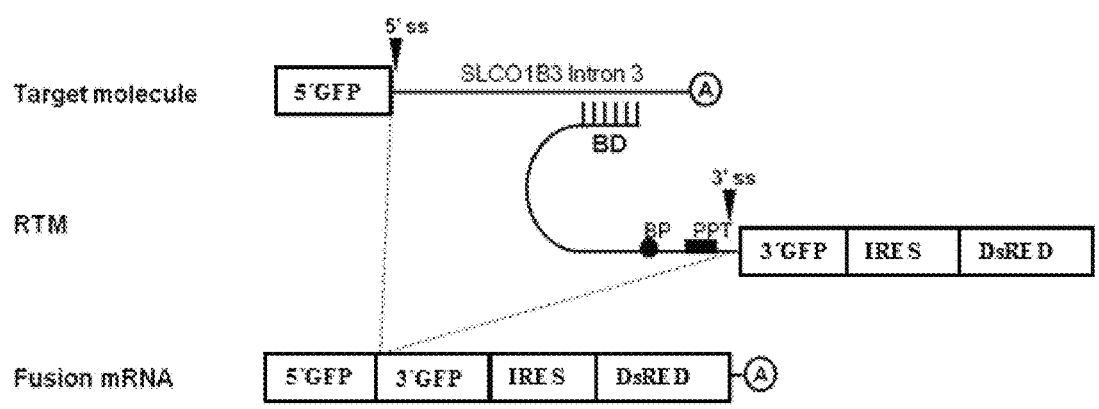

This application is a National Stage Application of International Application Number PCT/EP2013/072823, filed Oct. 31, 2013; which claims priority to Great Britain Application No. 1219762.0, filed Nov. 2, 2012; both of which are incorporated herein by reference in their entirety.

The Sequence Listing for this application is labeled "SeqList-08Dec.16-ST25.txt", which was created on Dec. 8, 2016, and is 13KB. The entire content is incorporated herein by reference in its entirety.

FIELD OF THE INVENTION

The present invention pertains to a novel pre-mRNA trans-splicing molecule (RTM) comprising a binding region, which is complementary to a pre mRNA of a tumor associated gene, and a coding domain which encodes for a suicide gene. Specific embodiments of the present invention relate to RTMs which mediate trans-splicing of a suicide gene, such as thymidine kinase from herpes simplex virus (HSV-tk), with the pre mRNA of the squamous cell carcinoma associated gene solute carrier organic anion transporter family member 1B3 (SLCO1B3). The invention provides RTMs which selectively kill cells expressing SLCO1B3 and which are thus useful in the treatment of cancer, specifically squamous cell carcinoma associated with epidermolysis bullosa. Also provided are methods, kits and pharmaceutical compositions relating to the RTMs in accordance with the invention.

DESCRIPTION

Most strategies for tumor elimination focus on the toxin-mediated cell death induction in tumor cells. A transgene encoding a toxin is delivered into the tumor cells leading to the subsequent cell death of the cells. Inefficient expression of the therapeutic gene due to hurdles in drug delivery and the targeting specificity of tumor cells remain the current obstacles of this technology up to date. One of the most established suicide genes is the thymidine kinase from herpes simplex virus (HSV-tk). This enzyme exhibits a high substrate affinity for the nucleoside analogue ganciclovir (GCV). The prodrug ganciclovir is converted into the metabolite GCV triphosphate (GCVTP) resulting in an intracellular toxic effect. Upon phosphorylation, GCV is incorporated into the replicating DNA leading to inhibition of DNA polymerization and finally to cell death by apoptosis.

RNA trans-splicing is a technology to deliver genetic information into a target mRNA by exploiting the cell's endogenous spliceosome. The trans-splicing reaction is facilitated by RNA trans-splicing molecules (RTMs) consisting of a binding domain (BD) for gene targeting, a splicing domain for efficient trans-splicing and a coding domain comprising the sequence to introduce. RTM binding to the target pre-mRNA induces specific trans-splicing between both molecules resulting in a new gene product consisting of the endogenous mRNA and the coding sequence provided by the RTM.

This system was already applied in vitro and in vivo to correct mutated genes in several genetic diseases, such as epidermolysis bullosa (EB), cystic fibrosis, hemophilia A or spinal muscular atrophy. In addition, SMaRT can be utilized to produce high levels of therapeutic proteins and antibodies in vivo by generating chimeric molecules.

Due to the fact that RTMs provide cell specific expression by binding to a defined target gene, RNA trans-splicing was also considered for cancer gene therapy. First, Puttaraju et al (Spliceosome-mediated RNA trans-splicing as a tool for gene therapy. Puttaraju M, Jamison S F, Mansfield S G, Garcia-Blanco M A, Mitchell L G. Nat Biotechnol. 1999 March; 17(3):246-52.) demonstrated accurate trans-splicing between human chorionic gonadotropin gene 6 and an RTM in vivo and in vitro. However, for a successful clinical application of suicide RTMs in EB cancer the efficiency and specificity have to be improved in order to provide increased cell killing ability with few side effects. Therefore, the inventors evaluated RTMs containing the clinically approved HSV-TK/GCV system. In a double transfection system the inventors analysed RTMs targeting the carrier organic anion transporter family member 1B3 (SLCO1B3), a marker gene associated with various human cancers including colorectal adenocarcinomas, breast and lung cancer and most important RDEB-SCC. The over expression of SLCO1B3 was also confirmed by the inventors using semi-quantitative real time PCR and microarray analysis (data not shown).

In view of the above described flaws in the background art, the objective of the present invention is to provide a new therapeutic strategy to target proliferative diseases, in particular squamous cell carcinoma associated with epidermolysis bullosa, by the introduction of a suicide gene which allows for the selective killing of malignant cells at the same time excluding healthy tissues.

In a first aspect of the present invention, the above objective is solved by providing a RNA trans-splicing molecule (RTM), comprising at least one binding domain, at least one splicing domain and at least one coding domain, characterized in that the coding domain comprises a suicide gene sequence.

The elimination of tumour cells faces a big challenge due to multiple issues. One such hurdle is the discrimination between normal and malignant cells. The variable gene expression pattern of these cell populations opens new avenues towards a more cell specific therapy approach. In this work the inventors described the possibility to target overexpressed genes in tumour cells using the mRNA-based method Spliceosome Mediated RNA Trans-Splicing (SMaRT). RNA trans-splicing can be used as a cell- and gene-specific technique to induce toxin mediated cell death predominantly in tumour cells. Targeting tumour specific marker genes will provide higher cell specificity, reducing side effects common in conventional toxin-based applications. The introduction of an RTM carrying a toxin into target cells should lead to a cell specific trans-splicing reaction between the tumour marker gene and the RTM, resulting in a gene-toxin fusion mRNA. The subsequent expression of the fusion protein develops the impact of the toxin that kills the cell.

In a first preferred embodiment of the invention, the RTM is designed to comprise only a minimal number of start codons (ATG) or cryptic splice sites upstream of the coding domain containing the sequence of the suicide gene. This is necessary to reduce undesirable expression of the suicide gene without being fused to the target exon sequence via trans-splicing. Such events can either occur by direct in-frame translation of the RTM from an unwanted start codon or because cryptic splice sites within the RTM yield into splicing with other cellular mRNAs or cis splicing events which then again lead to the uncontrolled expression of the suicide gene. Specifically it is preferred that the RTM of the invention does not comprise any start codons or cryptic splice sites upstream or within the binding domain of the RTM or most preferably, wherein the RTM does not comprise any start codons or cryptic splice sites upstream of the coding sequence of the suicide gene. The term cryptic splice site denotes any splice site which is not in direct proximity to the coding domain and which therefore might result in trans- or cis-splicing products which are not dependent on the selective binding of the binding domain to its target (complementary) sequence and which might express the suicide gene. Such unselective RTMs are in a preferred embodiment not included in the invention, since they could induce cell death without any selectivity to the target cell.

In one embodiment the pre-mRNA trans-splicing molecule (RTM) in accordance with the invention, comprises a) at least one binding domain that targets binding of the nucleic acid molecule to a pre-mRNA expressed within a cell; b) at least one splicing domain containing motifs necessary for the trans-splicing reaction to occur, and c) at least one coding domain, wherein said coding domain. The general design, construction and genetic engineering of RTMs and demonstration of their ability to successful induce spliceosome mediated transsplicing reactions within the cell are described in detail in U.S. Pat. Nos. 6,083,702, 6,013,487, 7,399,753 and 6,280,978 as well as patent applications with the U.S. Ser. Nos. 09/756,095, 09/756,096 09/756,097 and 09/941,492, the disclosures of which are incorporated by reference in their entirety herein.

In brief, an RTM molecule is designed to carry a binding domain (BD) complementary to and in antisense orientation to an intron sequence of the target pre-mRNA, to suppress target cis-splicing while enhancing trans-splicing between the RTM and the target (Mansfield et al. 2000). An RTM further consists of a splicing domain, comprising a strong conserved branch point (BP) sequence, a polypyrimidine tract (PPT), and a 3' acceptor splice site (ss). A spacer sequence separates the splicing domain from the target binding domain. And finally an RTM comprises a coding domain with the part of the wild type coding sequence to be trans-spliced to the target pre-mRNA. The coding domain can be a single exon, multiple exons or an entire coding sequence. In the context of the present invention, the coding domain preferably is a complete coding sequence of a suicide gene, however, without the translation initiation codon (start codon: ATG). The BD brings specificity to trans-splicing by binding specifically to the endogenous target pre-mRNA, whereas the splicing and coding domains provide essential consensus motifs that are recognized by the spliceosome and make the trans-splicing reaction actually happen. The use of BP and PPT follows consensus sequences which are needed for performance of the two phosphoryl transfer reaction involved in cis-splicing and, presumably, also in trans-splicing (Kramer 1996). These reactions, catalyzed by the spliceosome, must excise the introns precisely in order to produce functional mRNAs. In a manner similar to the RNA cis-splicing processes, the binding domain and splicing domain sequences of the RTM RNA are excised after trans-splicing and are not retained in the reprogrammed final mRNA products.

The methods of the invention encompass contacting the RTMs of the invention with a target pre-mRNA, under conditions in which a portion of the RTM is trans-spliced to a portion of the target pre-mRNA to form a novel RNA molecule that is further processed and expressed in the cell.

The target binding domain of the RTM endows the RTM with a binding affinity for the target pre-mRNA. As used herein, a target binding domain is defined as any molecule, i.e., nucleotide, protein, chemical compound, etc., that confers specificity of binding and anchors the pre-mRNA closely in space to the synthetic RTM so that the spliceosome processing machinery of the nucleus can trans-splice a portion of the synthetic RTM to a portion of the pre-mRNA.

The target binding domain of the RTM may contain multiple binding domains which are complementary to and in anti-sense orientation to the targeted region of the selected target pre-mRNA. The target binding domains may comprise up to several thousand nucleotides. In preferred embodiments of the invention the binding domains may comprise at least 10 to 30 and up to several hundred or more nucleotides. The specificity of the RTM may be increased significantly by increasing the length of the target binding domain. For example, the target binding domain may comprise several hundred nucleotides or more. Absolute complementarity, although preferred, is not required. A sequence "complementary" to a portion of an RNA, as referred to herein, means a sequence having sufficient complementarity to be able to hybridize with the target pre-mRNA, forming a stable duplex. The ability to hybridize will depend on both the degree of complementarity and the length of the nucleic acid (See, for example, Sambrook et al., 1989, Molecular Cloning, A Laboratory Manual, 2d Ed., Cold Spring Harbor Laboratory Press, Cold Spring Harbor, N.Y.). Generally, the longer the hybridizing nucleic acid, the more base mismatches with an RNA it may contain and still form a stable duplex. One skilled in the art can ascertain a tolerable degree of mismatch or length of duplex by use of standard procedures to determine the stability of the hybridized complex.

Binding may also be achieved through other mechanisms, for example, through triple helix formation, aptamer interactions, antibody interactions or protein/nucleic acid interactions such as those in which the RTM is engineered to recognize a specific RNA binding protein, i.e., a protein bound to a specific target pre-mRNA.

3' RTM molecules also contain a 3' splice region that includes a branchpoint sequence and a 3' splice acceptor AG site and/or a 5' splice donor site. The 3' splice region may further comprise a polypyrimidine tract. 5' RTMs contain a 5' splice site region, including a GU splice donor site. Consensus sequences for the 5' splice donor site and the 3' splice region used in RNA splicing are well known in the art (See, Moore, et al., 1993, The RNA World, Cold Spring Harbor Laboratory Press, p. 303-358). In addition, modified consensus sequences that maintain the ability to function as 5' donor splice sites and 3' splice regions may be used in the practice of the invention. Briefly, the 5' splice site consensus sequence is AG/GURAGU (where A=adenosine, U=uracil, G=guanine, C=cytosine, R=purine and/=the splice site). The 3' splice site consists of three separate sequence elements: the branchpoint or branch site, a polypyrimidine tract and the 3' consensus sequence (YAG). The branch point consensus sequence in mammals is YNYUR<u>A</u>C (Y=pyrimidine; N=any nucleotide). The underlined A is the site of branch formation. A polypyrimidine tract is located between the branch point and the splice site acceptor and is important for different branch point utilization and 3' splice site recognition. Recently, pre-mRNA introns referred to as U12-dependent introns, many of which begin with the dinucleotide AU and end in the dinucleotide AC, have been described. U12-dependent intron sequences as well as any sequences that function as splice acceptor/donor sequences may also be used to generate the RTMs of the invention.

A spacer region to separate the RNA splice site from the target binding domain may also be included in the RTM. The spacer region may be designed to include features such as (i) stop codons which would function to block translation of any unspliced RTM and/or (ii) sequences that enhance trans-splicing to the target pre-mRNA.

In accordance with the present invention, a preferred RTM is, wherein said suicide gene sequence encodes for a protein that when expressed in a cell induces cell-death or inhibits cell-growth or -division. The suicide gene used in the present invention preferably is a prodrug activating enzyme which converts a non-toxic prodrug of, e.g. an anticancer agent, to the toxic version of the anticancer agent. Exemplary suicide genes include the genes encoding herpes simplex type 1 thymidine kinase (HSV-TK) and cytosine deaminase (CD). HSV-TK converts non-toxic gancyclovir (GCV) to toxic phosphorylated metabolite, and CD converts non-toxic 5-fluorocytosine (5-FC) to toxic 5-fluorouracil (5-FU). An additional example of a suicide gene is thymidine kinase of Varicella Zoster virus (VZV-tk) (disclosed in Lacey S F et al, Analysis of mutations in the thymidine kinase genes of drug-resistant varicella-zoster virus populations using the polymerase chain reaction, J. Gen. Viol. 72 (PT 3), 623-630, 1991). A further example is Streptolysin O. (Yang W S, Park S O, Yoon A R, Yoo J Y, Kim M K, Yun C O, et al. Suicide cancer gene therapy using pore-forming toxin, streptolysin O. Mol Cancer Ther 2006; 5:1610-9.) or Diphteria toxin as used in Puttaraju et al. (see above).

Thus, the tumor cells that are selectively targeted by the RTM of the invention are more susceptible and sensitive to the prodrug treatment, since they are exposed to toxic metabolites as a result of prodrug activation. In this regard, it has been discovered that activated toxic metabolites can passively diffuse to neighbouring tumor cells to further enhance tumor killing. This is called a "bystander effect". The bystander effect plays an important role in the eradication of surrounding tumor cells which might not have been able to be targeted by an RTM of the invention. This is caused by transmission of the activated prodrug from the RTM treated tumor cells (which in the case of transduction methods may be only a small fraction of total tumor mass) to non-treated tumor cells. In the HSVtk/GCV system, the activated GCV is not membrane permeable because of its highly charged phosphate groups. However, it can be transferred to uninfected cells via the gap junctions or through the exchange of apoptotic vesicles that kill the surrounding untransduced tumor cells.

The prodrugs useful in the methods of the present invention are any that can be converted to a toxic product, i.e., toxic to tumor cells. A preferred prodrug is ganciclovir, which is converted in vivo to a toxic compound by HSV-tk (Chen et al., Cancer Res. 1996, 56: 3758-3762). Other representative examples of prodrugs include acyclovir, FIAU [1-(2-deoxy-2-fluoro-β-D-arabinofuranosyl)-5-iodouracil] (FIALURIDINE™, Moravek Biochemicals and Radiochemicals), 6-methoxypurine arabinoside (converted by VZV-tk), and 5-fluorocytosine (converted by cytosine deaminase) (5-fluorocytosine, Roche).

Prodrugs, may be readily administered to patients by physicians having ordinary skill in the art. Using methods known in the field, such physicians would also be able to determine the most appropriate dose and route for the administration of the prodrug. For example, ganciclovir is preferably administered systemically (e.g. orally or parenterally) in a dose of about 1-20 mg/day/kg body weight; acyclovir is administered in a dose of about 1-100 mg/day/kg body weight, and FIAU is administered in a dose of about 1-50 mg/day/kg body weight.

In a preferred embodiment of the invention, the RTM comprises at least one binding domain which is complementary to a tumor associated pre-mRNA. A tumor associated pre-mRNA is a precursor mRNAs transcribed from tumor marker genes, i.e. genes which are selectively expressed in tumors opposed to healthy cells. In the art four known categories of tumor associated genes are known. (I) mutated antigens develop during tumor-genesis by point mutations or translocations within the tumor cells. Those antigens are strictly tumor specific. (II) cancer/germline antigens are usually expressed solely within the germline of an adult organism and not in healthy somatic tissue. In cancer cells however, due to the loss of epigenetic regulation, germline specific genes can be activated. (III) differentiation antigens are expressed in tumors and their healthy progenitor cells, (IV) overexpressed tumor associated genes show only minor expression in healthy cells whereas in a tumor those proteins are strongly activated.

In a further preferred embodiment in accordance with the present invention an RTM is provided comprising a nucleic acid sequence according to any one of SEQ ID Nos. 1 to 6. Most preferred is that the RTM of the invention comprises a sequence according to any one of SEQ ID Nos. 4 to 6. These are the preferred binding domains for the RTMs of the invention. Also comprised in the context of the invention is an RTM having a binding domain comprising a nucleic acid sequence with at least 85%, preferably 90%, most preferably 95%, 96%, 97%, 98% or 99% sequence identity to any one of the sequences shown in SEQ ID Nos. 4 to 6.

In preferred embodiments in accordance with the invention said tumor associated pre-mRNA is a pre-mRNA associated with a tumor selected from solid tumors, especially cancers of the gastrointestinal tract, the pancreas, breast, stomach, cervix, bladder, kidney, prostate, ovaries, endometrium, lung, brain, skin, such as melanoma, Kaposi's sarcoma, squamous cell carcinoma, cancers of head and neck, malignant pleural mesothelioma, lymphoma or multiple myeloma, glioblastoma and liquid tumors especially leukemias such as CML or ALL. Most preferred in the context of the invention is a pre-mRNA which is associated to squamous cell carcinoma in association with epidermolysis bullosa.

In one specific embodiment said tumor associated pre-mRNA is solute carrier organic anion transporter family member 1B3 (SLCO1B3). SLCO1B3 mediates the Na(+)-independent uptake of organic anions such as 17-beta-glucuronosyl estradiol, taurocholate, triiodothyronine (T3), leukotriene C4, dehydroepiandrosterone sulfate (DHEAS), methotrexate and sulfobromophthalein (BSP). The encoded protein is a transmembrane receptor that mediates the sodium-independent uptake of endogenous and xenobiotic compounds and plays a critical role in bile acid and bilirubin transport. Six splice variants are known for SLCO1B3. The gene is located on the forward strand of Chromosome 12: 20,963,636-21,243,040.

Preferred in accordance with the present invention is that the binding domain of the RTM comprises a sequence complementary to an intron of gene SLCO1B3. However, in further embodiments of the invention the binding domain may also be exonic, or mixed intronic/exonic. Examples of such mixed binding domains for RTMs are found in e.g. EP 2 151 248.

Preferred is that the intron is an intron that follows at least the first protein coding exon, thus, e.g. intron, 3, 4, 5, 6, 7, 8, 9, 10, 11, 12, 13, or 14, most preferentially intron 3 of SLCO1B3. Thus, the RTM in accordance with the present invention preferably produces upon trans-splicing in a cell a trans-spliced mRNA which is composed of the first exon (exon 3) of SLCO1B3 and the coding sequence of the suicide gene (e.g. HSV-TK) without the suicide gene's start codon. However, this shall not exclude that the RTM of the invention furthermore contains sequences within its binding domain which are complementary to exon sequences of the targeted gene, thus preferably exonic sequences of the SLCO1B3 gene.

Even more preferred is an RTM in accordance with the present invention, having a binding domain binding to a sequence (selectively) which is at least 80, 85, 90, 95, 96, 97, 98, 99 or 100% identical to the nucleotide sequence between nucleotides 1075 and 1100 of intron 3 of the gene sequence of SLCO1B3, preferably between nucleotides 1050 and 1100 of intron 3 of the gene sequence of SLCO1B3, most preferably between nucleotides 1012 and 1118 of intron 3 of the gene sequence of SLCO1B3. As also described above, the binding sequence in accordance with the RTM of the present invention in one additional preferred embodiment is has a modified sequence. The modification compared to the original binding domain is that start codons (at least those being in frame with the coding sequence of the suicide gene) are removed and/or that any cryptic splice sites are removed.

One additional embodiment of the invention relates to an RTM as described herein, wherein the RTM further comprises at least one safety sequence in said splicing domain and/or at least one sequence complementary to neighbouring exon sequences. Said "safety sequence" is incorporated into the spacer, binding domain, or elsewhere in the RTM to prevent non-specific trans-splicing. This is a region of the RTM that covers elements of the 3' and/or 5' splice site of the RTM by relatively weak complementarity, preventing non-specific trans-splicing. The RTM is designed in such a way that upon hybridization of the binding/targeting portion(s) of the RTM, the 3' and/or 5' splice site is uncovered and becomes fully active. Such "safety sequences" comprises one or more complementary stretches of cis-sequence (or could be a second, separate, strand of nucleic acid) which binds to one or both sides of the RTM branch point, pyrimidine tract, 3' splice site and/or 5' splice site (splicing elements), or could bind to parts of the splicing elements themselves. This "safety" binding prevents the splicing elements from being active (i.e. block U2 snRNP or other splicing factors from attaching to the RTM splice site recognition elements). The binding of the "safety sequence" may be disrupted by the binding of the target binding region of the RTM to the target pre-mRNA, thus exposing and activating the RTM splicing elements (making them available to trans-splice into the target pre-mRNA).

Further preferred is an RTM according to the present invention, wherein the binding of the nucleic acid molecule to the target pre-mRNA is mediated by complementarity (i.e. based on base-pairing characteristics of nucleic acids), triple helix formation (as described in, for example, Suzuki T. Targeted gene modification by oligonucleotides and small DNA fragments in eukaryotes. Front Biosci. 2008 Jan. 1; 13:737-44. Review. Dang N, Klingberg S, Man P, Murrell D F. Review of collagen VII sequence variants found in Australasian patients with dystrophic epidermolysis bullosa reveals nine novel COL7A1 variants. J Dermatol Sci. 2007 June; 46(3):169-78. Review), or protein-nucleic acid interaction (as described in the respective literature).

Another aspect of the present invention relates to an RTM according to the present invention, wherein the exon to be trans-spliced comprises naturally occurring or artificially introduced stop-codons and/or a stem-forming structure in order to provide an RNAi-like effect.

Furthermore preferred in the context of this invention is that the RTM comprises further a 3'UTR improving trans-splicing efficiency, expression or RNA stability. Additional features can be added to the RTM molecule, such as polyadenylation signals to modify RNA expression/stability, or 5' splice sequences to enhance splicing, additional binding regions, "safety"-self complementary regions, additional splice sites, or protective groups to modulate the stability of the molecule and prevent degradation. In addition, stop codons may be included in the RTM structure to prevent translation of unspliced RTMs. Further elements such as a 3' hairpin structure, circularized RNA, nucleotide base modification, or synthetic analogs can be incorporated into RTMs to promote or facilitate nuclear localization and spliceosomal incorporation, and intra-cellular stability.

The RTM in accordance with the present invention is a nucleic acid molecule, such as DNA, RNA, DNA/RNA hybrid, or nucleic acid analog molecule.

Another aspect of the present invention then relates to a recombinant expression vector, comprising a RTM according to the present invention as above. A vector within the meaning of the present invention is a nucleic acid, which is capable of being introduced or of introducing nucleic acid as comprised into a cell. It is preferred that the RTMs encoded by the introduced nucleic acid are expressed within the cell upon introduction of the vector. Preferably, said vector is a eukaryotic expression vector, preferably a vector made of virus derived sequences. Further preferred is a vector of the present invention, wherein said vector furthermore comprises skin-cell and preferably keratinocyte specific regulatory elements in order to direct transgene expression.

Suitable expression vectors for in vitro or in vivo expression can be found in the literature. These vectors can also be easily modified by the person of skill in the art in order to be applied in the methods of the present invention. The expression vectors usually contain all genetic elements that are necessary for the production of a specific RTM molecule. In some embodiments of the present invention, the expression vectors according to the present invention can have the form of a "transgene", i.e. an expression element in, for example, a suitable vector that is designed for an expression and particularly an inducible and/or controllable expression in vivo. Accordingly, the transgene comprises nucleic acids of the present invention together with certain genetic control elements for the expression as discussed herein.

In a preferred embodiment the vector of the present invention comprises plasmids, phagemids, phages, cosmids, artificial mammalian chromosomes, knock-out or knock-in constructs, viruses, in particular adenovirus, vaccinia virus, lentivirus (Chang, L. J. and Gay, E. E. (20001) Curr. Gene Therap. 1: 237-251), Herpes simplex virus (HSV-1, Carlezon, W. A. et al. (2000) Crit. Rev. Neurobiol.; 14(1): 47-67), baculovirus, retrovirus, adeno-associated-virus (AAV, Carter, P. J. and Samulski, R. J. (2000) J. Mol. Med. 6: 17-27), rhinovirus, human immune deficiency virus (HIV), filovirus and engineered versions thereof (see, for example, Cobinger G. P. et al (2001) Nat. Biotechnol. 19: 225-30), virosomes, "naked" DNA liposomes, and nucleic acid coated particles, in particular gold spheres. Particularly preferred are viral vectors like adenoviral vectors or retroviral vectors (Lindemann et al. (1997) Mol. Med. 3: 466-76 and Springer et al. (1998) Mol. Cell. 2: 549-58). Liposomes are usually small unilamellar or multilamellar vesicles made of neutral cationic and/or anionic lipids, for example, by ultrasound treatment of liposomal suspensions. The DNA can, for example, be ionically bound to the surface of the liposomes or internally enclosed in the liposome. Suitable lipid mixtures are known in the art and comprise, for example, cholesterol, phospholipide like, for example, phosphatidylcholin (PC), phosphatidylserin (PS) and the like, DOTMA (1,2-Dioleyloxpropyl-3-trimethylammoniumbromid) and DPOE (Dioleoylphosphatidylethanolamin) which both have been used on a variety of cell lines. Nucleic acid coated particles are another means for the introduction of nucleic acids into cells using so called "gene guns", which allow the mechanical introduction of particles into the cells. Preferably the particles are themselves inert, and therefore, are in a preferred embodiment made out of gold spheres.

In preferred embodiments of the present invention the herein described furthermore comprises skin-cell and preferably keratinocyte, fibroblast or endothelial cell specific regulatory elements for regulating transgene expression.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill. Preferred hist cells recombinant cells, preferably a recombinant skin cell such as a keratinocyte, fibroblast or endothelial cell, comprising an RTM-molecule or a recombinant expression vector in accordance with the present invention.

Transformation of appropriate cell hosts with a DNA construct of the present invention is accomplished by well-known methods that typically depend on the type of vector used. With regard to transformation of prokaryotic host cells, see, for example, Cohen et al (1972) Proc. Natl. Acad. Sci. USA 69, 2110, and Sambrook et al (1989) Molecular Cloning, A Laboratory Manual, Cold Spring Harbor Laboratory, Cold Spring Harbor, N.Y. Transformation of yeast cells is described in Sherman et al (1986) Methods In Yeast Genetics, A Laboratory Manual, Cold Spring Harbor, N.Y. The method of Beggs ((1978) Nature 275, 104-109) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Another aspect of the present invention then relates to a pharmaceutical preparation, comprising a physiologically acceptable carrier and the RTM-molecule according to the present invention, the recombinant expression vector according to the present invention, or the recombinant skin cell according to the present invention. Yet another aspect of the present invention then relates to an RTM-molecule according to the present invention, the recombinant expression vector according to the present invention, the recombinant skin cell according to the present invention, or the pharmaceutical preparation according to the present invention for use as a medicament.

In a specific embodiment, the term "pharmaceutically acceptable" means approved by a regulatory agency of the Federal or a state government or listed in the U. S. Pharmacopeia or other generally recognized pharmacopeia for use in animals, and more particularly in humans. The term "carrier" refers to a diluent, adjuvant, excipient, or vehicle with which the synthetic is administered. Examples of suitable pharmaceutical carriers are described in "Remington's Pharmaceutical sciences" by E. W. Martin.

In specific embodiments, pharmaceutical compositions are administered: (1) in diseases or disorders involving an absence or decreased (relative to normal or desired) level of an endogenous protein or function, for example, in hosts where the protein is lacking, genetically defective, biologically inactive or underactive, or under expressed; or (2) in diseases or disorders wherein, in vitro or in vivo, assays indicate the utility of synthetic RTMs that inhibit the function of a particular protein. The activity of the protein encoded for by the chimeric mRNA resulting from the synthetic RTM mediated trans-splicing reaction can be readily detected, e.g., by obtaining a host tissue sample (e.g., from biopsy tissue) and assaying it in vitro for mRNA or protein levels, structure and/or activity of the expressed chimeric mRNA. Many methods standard in the art can be thus employed, including but not limited to immunoassays to detect and/or visualize the protein encoded for by the chimeric mRNA (e.g., Western blot, immuno-precipitation followed by sodium dodecyl sulfate polyacrylamide gel electrophoresis, immunocytochemistry, etc.) and/or hybridization assays to detect formation of chimeric mRNA expression by detecting and/or visualizing the presence of chimeric mRNA (e.g., Northern assays, dot blots, in situ hybridization, and Reverse-Transcription PCR, etc.), etc. Alternatively, direct visualization of a reporter gene either encoded by the synthetic RTM or associated with an RTM may be carried out.

The present invention also provides for pharmaceutical compositions comprising an effective amount of a synthetic RTM or a nucleic acid encoding a synthetic RTM, and a pharmaceutically acceptable carrier. In a specific embodiment, it may be desirable to administer the pharmaceutical compositions of the invention locally to the area in need of treatment. This may be achieved by, for example, and not by way of limitation, local infusion during surgery, topical application, e. g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Or other control release drug delivery systems, such as nanoparticles, matrices such as controlled-release polymers, hydrogels. The RTM or synthetic RTM will be administered in amounts which are effective to produce the desired effect in the targeted cell. Effective dosages of the synthetic RTMs can be determined through procedures well known to those in the art which address such parameters as biological half-life, bioavailability and toxicity. The amount of the composition of the invention which will be effective will depend on the nature of the disease or disorder being treated, and can be determined by standard clinical techniques. In addition, in vitro assays may optionally be employed to help identify optimal dosage ranges.

The present invention also provides a pharmaceutical pack or kit comprising one or more containers filled with one or more of the ingredients of the pharmaceutical compositions of the invention optionally associated with such container (s) can be a notice in the form prescribed by a governmental agency regulating the manufacture, use or sale of pharmaceuticals or biological products, which notice reflects approval by the agency of manufacture, use or sale for human administration.

Any molecule of the invention, nucleic acid, expression vector, or cell is useful for the treatment of the disorders as described herein. Therefore any molecule of the present invention may be used as medicament or in the manufacture of a medicament. The molecule may be used by itself or combined with other molecule(s) of the invention or (a) known molecule(s).

Preferably, the medicament of the present invention can be administered directly into the patient, into the affected organ or systemically i.d., i.m., s.c., i.p. and i.v., or applied ex vivo to cells derived from the patient or a human cell line which are subsequently administered to the patient, or used in vitro to produce recombinant cells which are then re-administered to the patient. In preferred embodiments of the invention, subsequent to the administration of the RTM in accordance with the invention, a prodrug is administered to initiate the killing of the target cells.

The amino acid of the invention may be substantially pure, or contained in a suitable vector or delivery system. The nucleic acid may be DNA, cDNA, PNA, CNA, RNA or a combination thereof. Methods for designing and introducing such a nucleic acid are well known in the art. An overview is provided by e.g. Pascolo S. 2006; Stan R. 2006, or A Mandavi 2006 (see Mandavi A, Monk B J. Recent advances in human papillomavirus vaccines. Curr Oncol Rep. 2006 November; 8 (6): 465-72. Stan R, Wolchok J D, Cohen A D. DNA vaccines against cancer. Hematol Oncol Clin North Am. 2006 June; 20(3): 613-36. Pascolo S. Vaccination with messenger RNA. Methods Mol Med. 2006; 127:23-40). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun," may also be used.

The present invention thus provides a medicament that is useful in treating disorders of the skin or other epithelia, such as epidermolysis bullosa, cystic fibrosis, pachyonychia congenital, autoimmune diseases, such as psoriasis or neurodermitis, and cancers of the skin.

Another aspect of the present invention then relates to the use of an RTM according to the present invention, the recombinant expression vector according to the present invention, the recombinant skin cell according to the present invention, or the pharmaceutical preparation according to the present invention for the treatment of a disease selected from disorders of the skin or other epithelia, such as epidermolysis bullosa, cystic fibrosis, pachyonychia congenita, autoimmune diseases, such as psoriasis or neurodermitis, and cancers of the skin. Preferred is the use according to the present invention, wherein said medicament is applied to the skin. A respective method of treatment of a disease as above is also encompassed by the scope of the present invention.

The present formulation is one that is suitable for administration of the respective active compound, in particular an RTM of the present invention by any acceptable route such as topical, oral (enteral), nasal, ophthalmic, subcutaneous, intradermal, intramuscular, intravenous or transdermal. Preferably the administration is s.c., and most preferably topical. Administration may be by infusion pump.

Preferred diseases to be treated with the present invention are proliferative diseases, preferably cancerous diseases such as cancers of the skin, most preferably squamous cell carcinoma; or a disease selected from genetic disorders of the skin and of epithelia, such as epidermolysis bullosa, cystic fibrosis, pachyonychia congenita, immunological diseases, such as psoriasis or neurodermitis.

Thus one additional aspect of the present invention pertains to a method of treating or preventing a disease as described herein above. The method of treatment involves the administration of a RTM molecule to patient in need of such a treatment, and subsequently the administration of a pro-drug. The pro-drug will in cells wherein the trans-splicing reaction occurs initiate cell death or via the suicide gene.

Figure 1C:
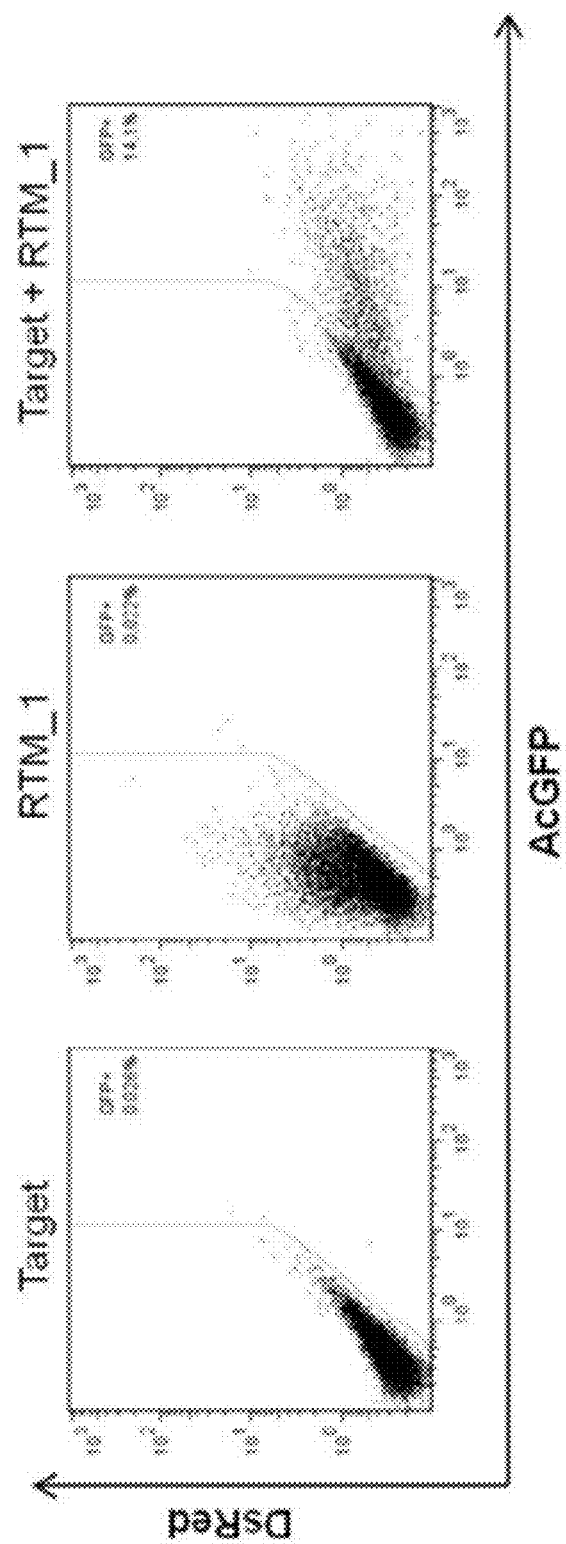

The present invention will now be further described in the following examples with reference to the accompanying figures and sequences, nevertheless, without being limited thereto. For the purposes of the present invention, all references as cited herein are incorporated by reference in their entireties. In the Figures and Sequences, FIGS. 1A-1C: Evaluation of a specific binding domain (BD) for efficient trans-splicing. FIG. 1A shows schematic diagram of the screening procedure used for evaluation of BDs. FIG. 1B shows the binding position of RTM_1 within the target intron 3 of SLCO1B3 (nt1012-nt1118) (SEQ ID NOs: 17-19). FIG. 1C shows an analysis of AcGFP expression by Flow cytometry in HEK293 cells transfected with the target molecule, RTM_1, or both target molecule +RTM¬ _1. Exclusively target molecule and RTM_1 co-transfected cells showed green fluorescence signal due to the fusion of both AcGFP split parts by RNA trans-splicing.

Figure 2A:
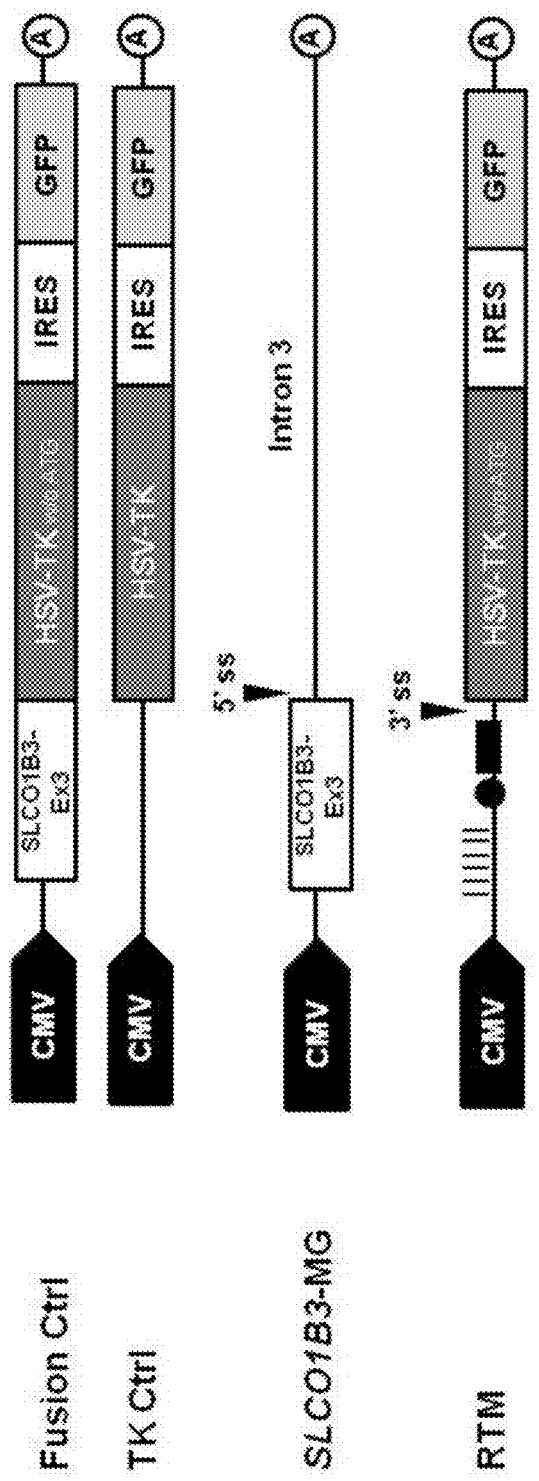
Figure 2B:
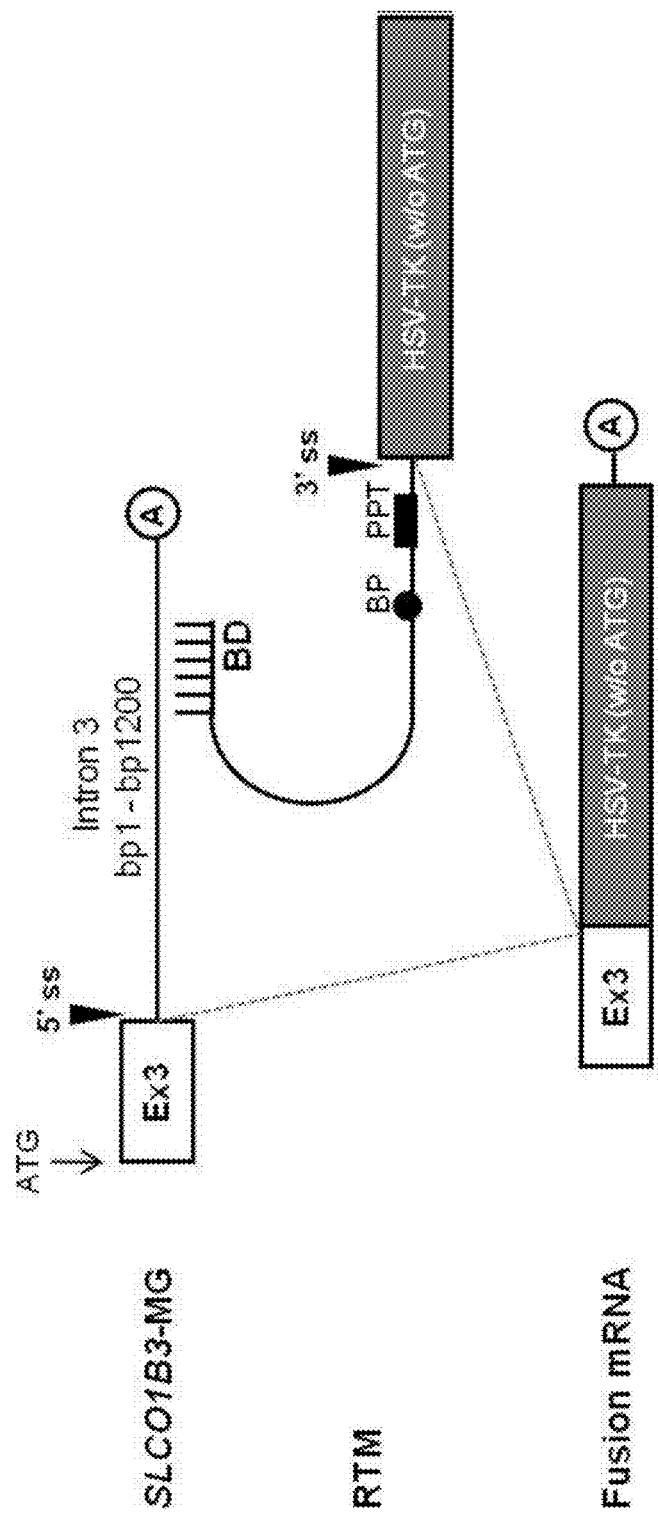

FIGS. 2A-2B: FIG. 2A shows constructs used in experimental procedure. FIG. 2B shows a schematic diagram of the double transfection system used for RTM evaluation. Correct trans-splicing of the RTM to the SLCO1B3-MG results in a fusion mRNA consisting of exon 3of SLCO1B3 and TK.

Figure 3A:
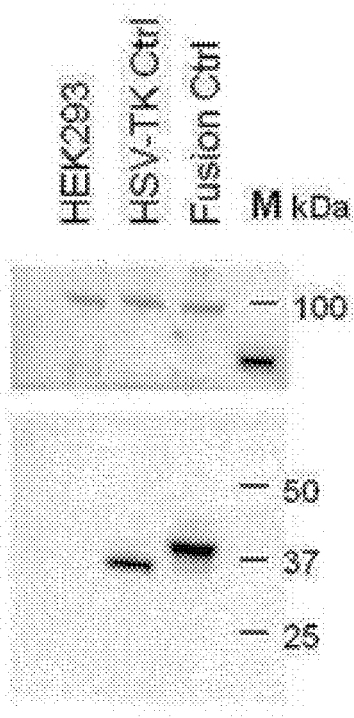
Figure 3B:
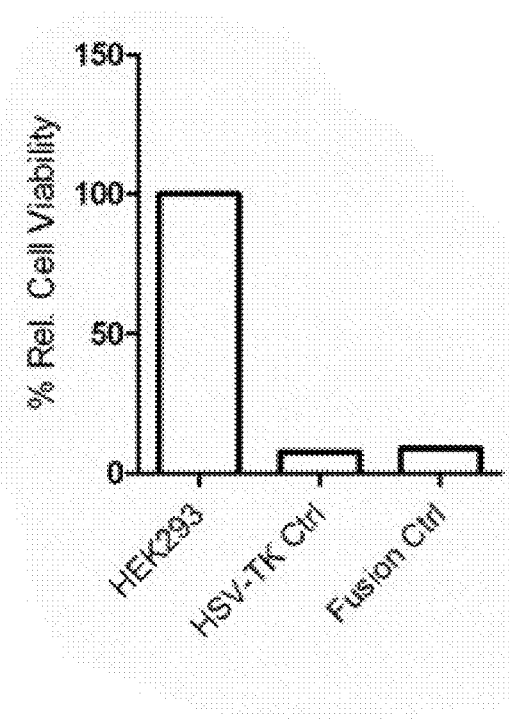

FIGS. 3A-3B: Expression and suicide gene activity of SLCO1B3-TK fusion construct. FIG. 3A shows Western blot analysis of HEK293AD cells 48h after transfection with HSV-TK (37kDa) or SLCO1B3-TK fusion (40kDa). Untreated cells served as negative control and α-actinin (100kDa) was used as loading control. FIG. 3B shows an MTT assay was performed to analyze the functionality of the expressed SLCO1B3-TK fusion protein representing the product created by specific RNA trans- splicing between the SLCO1B3-MG and the TK-RTM. The cell viability is presented as percentage relative to untransfected HEK293AD cells.

Figure 4A:
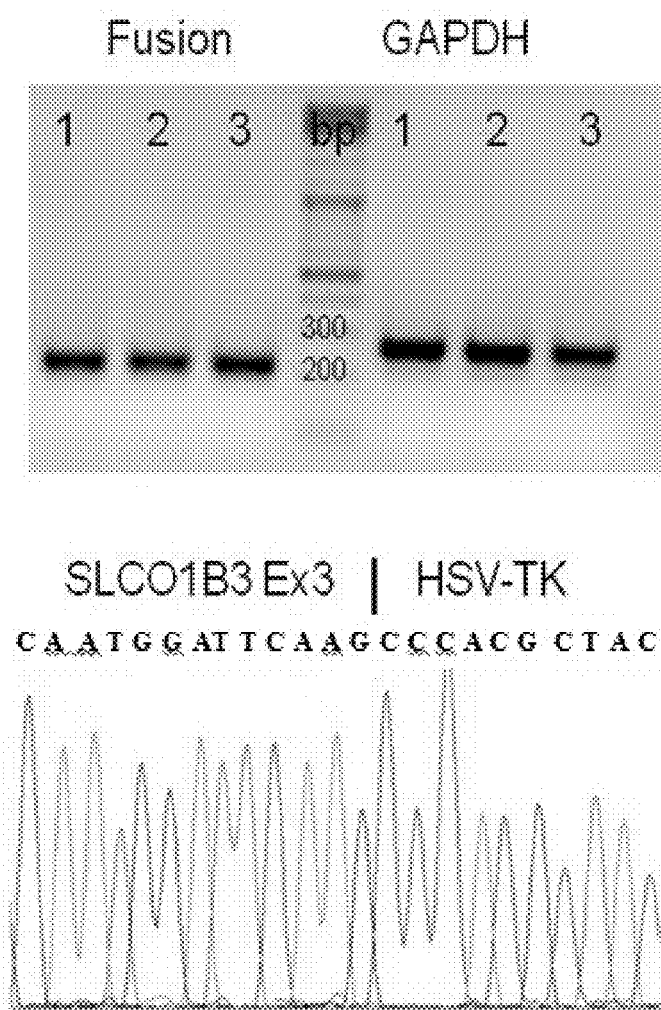
Figure 4B:
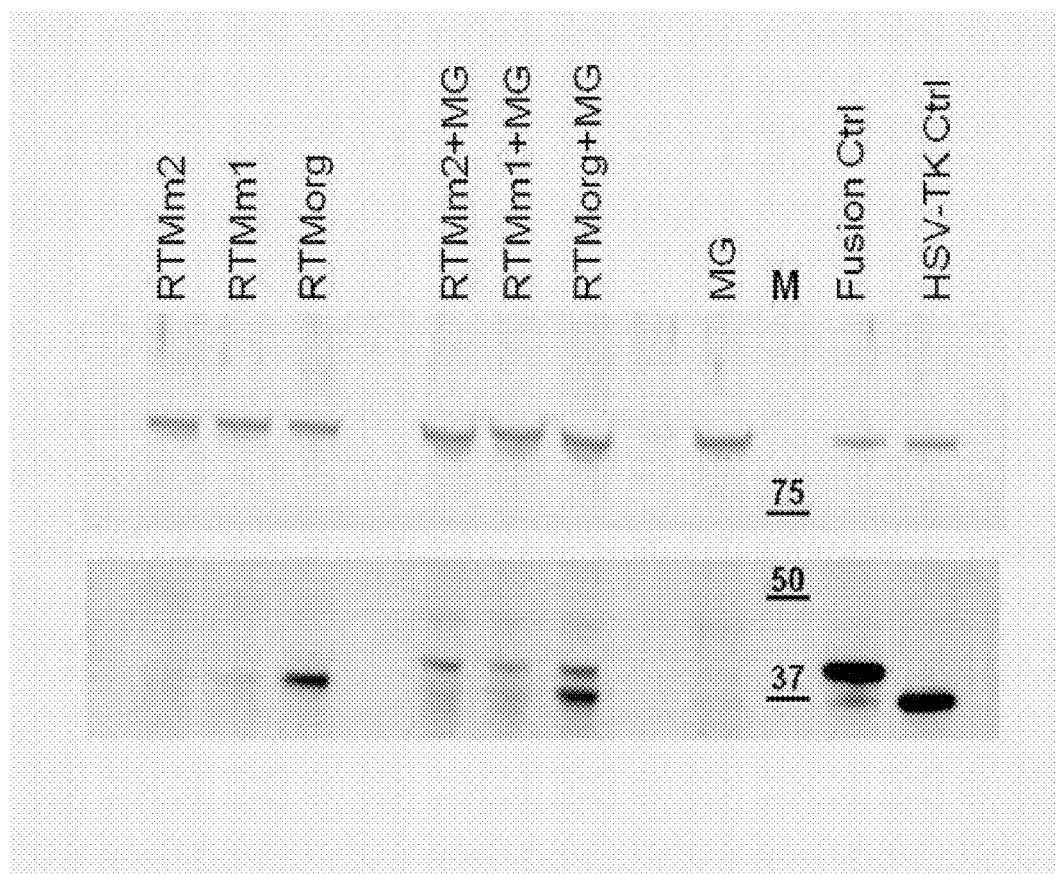

FIGS. 4A-4B: Detection of trans-Splicing. FIG 4A shows SqRT-PCR analysis of HEK293AD cells double transfected with the SLCO1B3-MG and RTMorg (1), RTMm1 (2), RTMm2 (3). The PCR product of the fusion mRNA of SCO1B3 and HSV-TK (205bp) is shown. GAPDH was used as housekeeping gene. PCR products were verified by direct sequencing, demonstrating correct trans-splicing between SLCO1B3-MG and the RTMs. FIG. 4B shows a Western blot analysis of single and co-transfected HEK293AD cells. α-Actinin staining (100kDa) served as loading control.

Figure 5A:
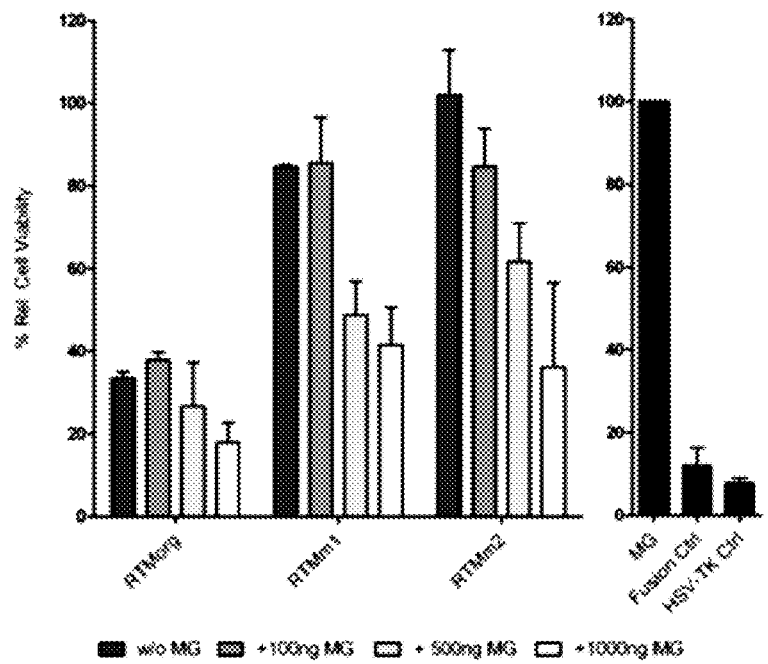
Figure 5B:
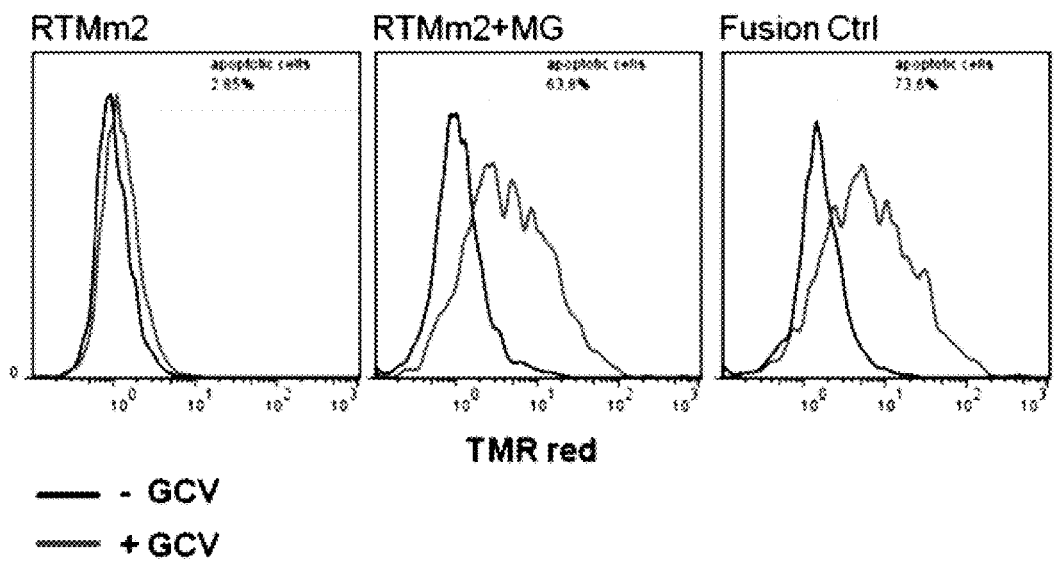
Figure 5C:
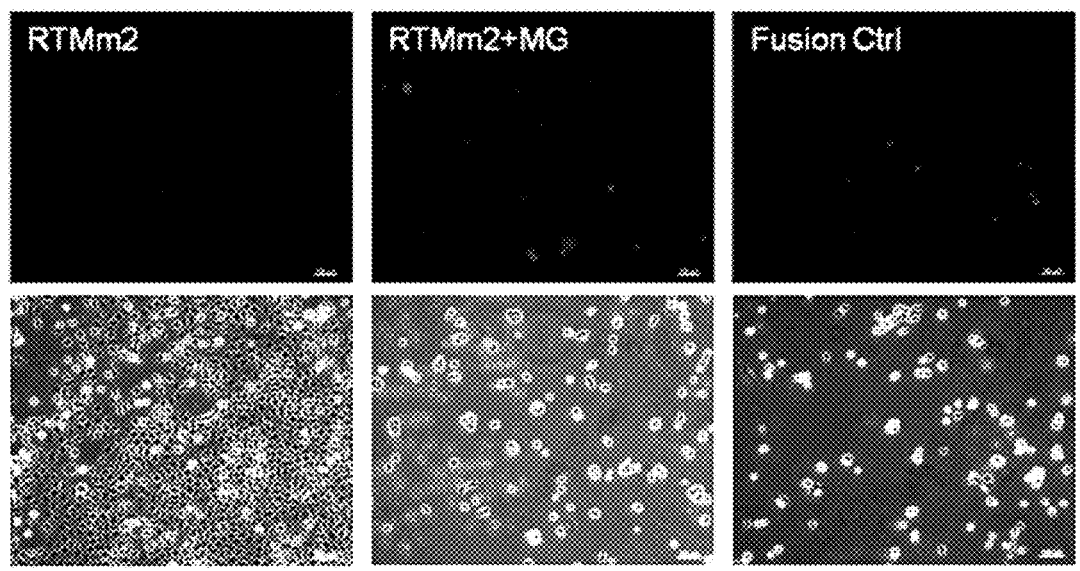

FIGS. 5A-5C: FIG. 5A shows a MTT assay performed to measure reduction in cell viability. 100ng of each RTM as well as different concentrations of the SLCO1B3 -MG (100ng, 500ng, 1000ng) were transfected in HEK293AD cells and treated with 100µM. HEK293AD cells, transfected with either the SLCO1B3-MG alone, the SLCO1B3-TK fusion or HSV-TK served as negative and positive controls, respectively. The mean±SD of two independent experiments is shown. Six replicates of each sample were measured in every experiment. The percentage of cell viability was calculated by the equation: (OD GCV-treated/OD GCV-untreated) ×100/ negative control (OD GCV-treated/OD GCV-untreated). FIG. 5B shows in situ cell death detection by TUNEL assay of RTMm2 and RTMm2 +MG treated HEK293AD-cells was assessed by flow cytometric analysis. The SLCO1B3-TK fusion served as positive control in the experiment. Overlay of TMR red positive cells is shown. Black line represents GCV untreated and red line GCV treated cell populations. FIG. 5C shows TMR red staining of apoptotic cells is shown by fluorescence microscopy analysis. The decline of cell number was visualized by light microscopy analysis.

Figure 6:
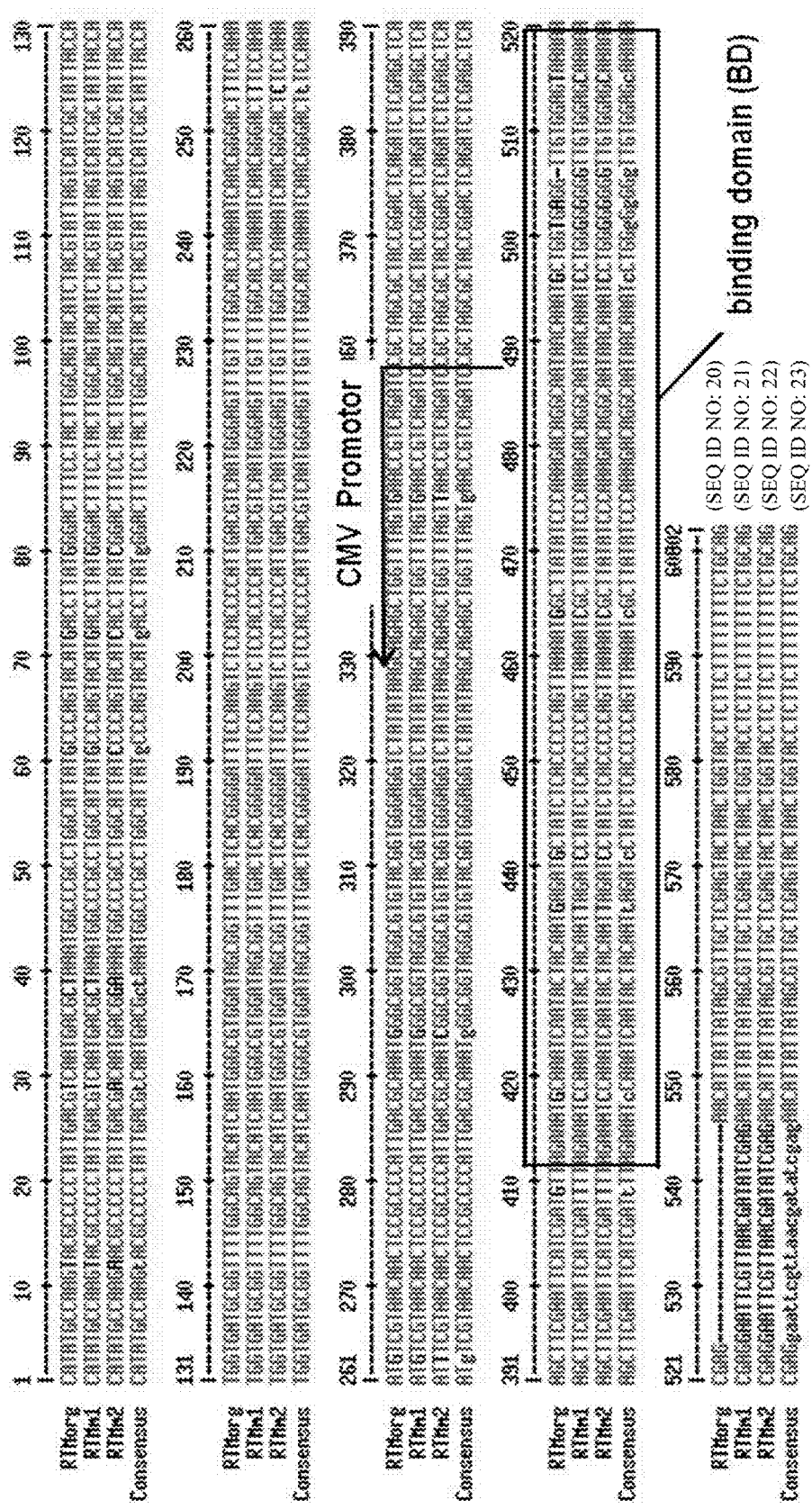

FIG. 6: Sequence alignment of different RTMs; RTMorg, RTMm1 and RTMm2 (SEQ ID NOs: 1-3 and SEQ ID NOs: 20-23).

SEQ ID NO: 1shows part of the sequence of RTMorg used in the alignment in FIG. 6. SEQ ID NO: 2 shows part of the sequence of RTMm1 used in the alignment in FIG. 6. SEQ ID NO: 3 shows part of the sequence of RTMm2 used in the alignment in FIG. 6. SEQ ID NO: 4 shows the binding domain sequence of RTMorg. SEQ ID NO: 5 shows the binding domain sequence of RTMm1. SEQ ID NO: 6 shows the binding domain sequence of RTMm2. SEQ ID NOs: 7 to 16 show primer sequences. SEQ ID NO: 17 shows intron 3 of the gene sequence of SLCO1B3. SEQ ID NO: 18 shows the binding domain sequence complementary to nucleotides 1012-1118 of intron 3 of SLCO1B3. SEQ ID NO: 19 shows the consensus sequence for the alignment of the binding domain and intron 3 of SLCO1B3. SEQ ID NOs: 20-23 show, respectively, the sequences of RTMorg, RTMm1, RTMm2, and the consensus sequence for the alignment of each of these three RTM sequences.

EXAMPLES

Example 1

Screening for an Efficient RTM Binding Domain

A binding domain (BD) screen helps to accelerate the construction of a highly efficient RTM for endogenous purposes. Using the fluorescence-based RTM screening procedure, the inventors were able to select a promising BD specific for intron 3 of SLCO1B3 out of a pool of randomly created BDs with various binding localizations within the target intron. Totally, 28 individual 3' RTMs were tested for their trans-splicing efficiency by flow cytometric analysis after co-transfection with the designed target molecule into HEK293AD cells (data not shown). Binding of the RTM specific to intron 3 of the target molecule induces the fusion of both AcGFP split sequence parts by 3' RNA trans-splicing, manifested in the expression of the full-length reporter in co-transfected cells. The intensity of the fluorescence signal and the amount of AcGFP expressing cells correlates with the trans-splicing efficiency of the transfected RTM (FIG. 1A). The analysis revealed RTM_1 (binding position in intron 3: nt1012-nt1118) as one of the most efficient RTMs and was thus selected for the initial tests in the thymidine kinase-based inducible cell death system (FIG. 1B+C).

Example 2

Trans-Splicing Between SLCO1B3-MG and TK-RTM

To further evaluate the specificity of RTMs in a suicide gene therapy approach the inventors cloned the BD from RTM_1 into the suicide RTM plasmid containing the thymidine kinase (TK) sequence from herpes simplex virus. The sequence upstream of the splicing domain was mutated in order to reduce potential cryptic splice sites and start codons, resulting in 3 different RTMs, termed RTMorg, RTMm1 and RTMm2. Detailed information on sequence modifications of the RTMs is provided in FIG. 6.

To mimic the endogenous RDEB-SCC situation in the experimental HEK293 cells, the inventors designed a mini-gene (MG) vector carrying exon 3 of the tumor marker gene SLCO1B3 as well as the first 1,200 bases of intron 3. HSV-TK and SLCO1B3-TK expressing vectors served as positive controls for the experimental procedure (FIG. 2A). In FIG. 2B a schematic diagram of the double transfection system is shown. Upon correct trans-splicing of the RTM with the MG pre-mRNA, a fusion mRNA of SCLO1B3 exon 3 and the HSV-TK is generated, encoding a fusion protein that is approximately 3 kDa larger than the original HSV-TK.

Example 3

The Fusion Protein of SLCO1B3-TK Exhibits Suicide Gene Activity

Prior to TK-RTM investigations the inventors determined whether the fusion protein, which results from the trans-splicing reaction between the SLCO1B3-MG and the TK-RTM, is expressed correctly and still possess its functionality as suicide gene. To this end, the inventors created the chimeric cDNA of SLCO1B3 exon 3 and the HSV-TK and confirmed its expression in whole cell lysates in HEK293AD cells by Western blot analysis (FIG. 3A). The SLCO1B3-TK fusion protein was detected at the predicted molecular weight of 40 kDa, 3 kDa larger than the original HSV-TK (37 kDa). Furthermore, the biologic activity of SLCO1B3-TK fusion protein was assessed in a MTT cell viability assay (FIG. 3B). HEK293AD cells were transfected with the plasmid HSV-TK or the fusion construct and treated with 100 µM GCV. Here the inventors demonstrated that the SLCO1B3-TK fusion protein is able to convert the pro-drug GCV into the toxic metabolite which induces cell death, resulting in reduction of cell viability similar to the original HSV-TK. Therefore, these data confirmed the functionality of the fusion construct, which will also result from the trans-splicing procedure in the experimental setup.

Example 4

Detection of SLCO1B3-TK Fusion on mRNA and Protein Level

To investigate accurate trans-splicing between the SLCO1B3-MG and each individual RTM the inventors first performed sqRT-PCR. The inventors detected the correct fusion mRNA in all 3 co-transfected cell populations represented by a 205 bp PCR product shown on an agarose gel (FIG. 4A). Interestingly, no significant difference in expression amount was observed (data not shown). In addition the inventors performed Western blot analysis to confirm the trans-splicing product also on the protein level. As shown in FIG. 4B the inventors maintained a high background expression of the HSV-TK in cells transfected with the RTMorg in contrast to the improved RTMs RTMm1 and m2. Furthermore, double transfection of the target and each individual RTM revealed that RTMorg showed the trans-spliced fusion construct (40 kDa) as well as the background HSV-TK protein (37 kDa). However, hardly any background expression of the HSV-TK was observed in RTMm1 and RTMm2 transfected cells and the trans-spliced fusion protein was still expressed. This data indicate that the improvement of RTMs by sequence optimization is important in order to reduce unwanted expression of the HSV-TK.

Example 5

Suicide Gene Induction by RNA Trans-Splicing

The RNA-based methodology SMaRT provides gene and cell specificity, thereby reducing unwanted side effects accompanied by other toxin mediated cell death approaches. The cell death is mainly induced in cells expressing the upregulated tumour marker gene SLCO1B3. The expression of the fusion constructs on the protein level, shown in FIG. 4B, also correlated with the reduction of cell viability measured in MTT assays (FIG. 5A). Single transfection of RTMorg already demonstrated induction of apoptosis in HEK293AD cells, explainable by alternative start codons (ATGs) and splice sites upstream and within the BD. Due to this fact, alternative in frame TK proteins are probably expressed from the RTM vector leading to a toxicity effect of the RTM alone in treated cells. Moreover co-transfection of RTMorg and the SLCO1B3-MG showed low reduction in cell viability indicating reduced trans-splicing effects. However, the deletion of ATGs and possible cryptic splice sites within and upstream of the BD sequence of the RTM by site-directed mutagenesis reduced the RTM mediated side effects significantly. RTMm1 and RTMm2 showed only a minimal ability to induce apoptosis using 100 ng plasmid/transfection. Furthermore, the addition of different amounts of the SLCO1B3-MG (100 ng, 500 ng, 1000 ng) lead to the fusion of SLCO1B3 exon 3 of the MG with the TK of the RTM by trans-splicing and induced the expression of a functional SLCO1B3-TK fusion protein in transfected cells. Both RTMm1 and RTMm2 induced a clear decrease of the cell viability after MG addition in a dose dependent manner. Additionally, the transfection of HSV-TK and SLCO1B3-TK fusion protein expressing plasmids demonstrated a clear reduction of the cell viability in comparison to exclusively MG transfected HEK293AD cells (FIG. 5A).

The TUNEL assay performed on transfected HEK293AD cells underlined the reliability and functionality of the inducible cell death system by trans-splicing constructs (FIG. 5B). The co-transfection of SLCO1B3-MG (1µg) and RTMm2 (100 ng) into HEK293AD cells induced apoptosis in up to 63.8% of cells revealed by flow cytometry. This result is comparable with the lethality rate of cells reached with the SLCO1B3-TK fusion control vector. Fluorescence microscopy on SLCO1B3-MG and RTMm2 co-transfected cells revealed increased TMR red staining, correlating with the decrease of healthy cells (light microscopy) in comparison to RTMm2 single transfected cells.

Materials and Methods

RTM Screening Constructs

SLCO1B3 target molecule: The target molecule harbours the 5' coding region of AcGFP (nt1-nt336), a functional 5' splice site (ag/gtaag) and the nucleotides 4-1200 (first 3 nucleotides of intron 3 were removed to avoid the creation of a possible competitive 5'ss) of intron 3 of SLCO1B3. The intron 3 portion was amplified by PCR using the Gotaq DNA polymerase (Promega), genomic DNA of a healthy donor and an intron specific primer pair (fw: 5'-gatcgatatcgaatgggtttatattttcaaactaaaataagttaatggaaaattttt-3',(SEQ ID NO. 7; rv: 5'-gagagcggccgcgatttgaatatacatttctcaaaagaagacatacaaatagc-3' SEQ ID NO. 8) inserting the restriction sites for cloning. The PCR product was ligated into the expression vector pcDNA 3.1DN5-His-TOPO downstream of the 5' AcGFP sequence using the restriction sites for EcoRV and NotI. Gel-extractions of amplified PCR products were performed using the GFXTM PCR DNA and Gel Band Purification Kit (GE Healthcare). Plasmid preparations were performed using the Plasmid Mini Prep Kit from Sigma-Aldrich (St. Louis, Mo., USA), according to the manufacturer's protocol. Sequence analysis of all plasmids and PCR products was carried out using a 3130 ABI Prism automated sequencer and ABI PRISM dye terminator cycle sequencing kits (Applied Biosystems).

RNA trans-splicing molecule: The RTM backbone consists of a splicing domain, carrying a short spacer region and 3' splicing elements (branch point, polypyrimidine tract, 3' acceptor splice site) for efficient splicing, and a coding domain incorporated by the missing 3' coding sequence of AcGFP (nt337-nt720) and the full-length DsRED gene expressed under the translational control of an internal ribosomal entry site (IRES) [14,19]. The creation of a highly diverse RTM library specific for intron 3 of SLCO1B3 was performed according to Bauer et al. (Bauer et al. 2012 in press, wird noch eingefügt). The cloning procedure of the binding domain (BD) library includes the PCR amplification of the intron 3 portion of SLCO1B3, the fragmentation of the PCR products by sonication (~10 min on ice) and finally the cloning of the resulting end repaired (DNATerminator® End Repair Kit, Lucigen Corporation) fragments into the RTM vector, upstream of the splicing domain using the restriction site for HpaI.

Constructs for HSV-TK-Based Inducible Cell Death System

SLCO1B3 minigene: To simulate the endogenous trans-splicing scenario as closely as possible a SLCO1B3 mini gene (SLCO1B3-MG) was constructed, which consists of the first coding exon of SLCO1B3 (exon 3: 84 nucleotides) and the first 1200 bases of intron 3 due to the huge size of the entire intron (39,205 nucleotides). The exon/intron 3 region of SLCO1B3 was PCR amplified from genomic DNA of a healthy donor using Gotaq DNA polymerase (Promega) and a specific primer pair (fw: 5'-gatcaagcttatggaccaacatcaacatttgaataaaacagc-3' SEQ ID NO. 9, rv: 540 -gagagcgccgcgatttgaatatacatttctcaaaagaagacatacaaatagc-3' SEQ ID NO. 10). The resulting PCR product was cloned into the pcDNA 3.1D/V5-His-TOPO vector (Invitrogen) using the restriction sites for HindIII and NotI.

TK-RTMs: First, the most efficient binding domain (BD), evaluated in the fluorescence based screening system, was cloned into the pIRES2-AcGFP1 vector (Clontech) together with the 3' splicing elements using the restriction sites for EcoRI and PstI. The coding sequence (CDS) of thymidine kinase from herpes simplex virus (HSV-TK) without the start codon was amplified from the HAX1-targeting vector, kindly provided by Dr. Peckl-Schmid [20]. Prior to PCR amplification the PstI restriction site within the CDS of HSV-TK was mutated using the QuikChange Lightning site-directed mutagenesis kit (Stratagene), according to manufacturer's protocol. The inventors used a forward primer including a PstI (5'-ctagctgcagcccacgctactgcgggttta-3' SEQ ID NO. 11), a reverse primer including a BamHI restriction site (5'-gagagaggatcctcagttagcctcccccatctc-3' SEQ ID NO. 12) and Pfu turbo polymerase (Stratagene) for PCR amplification. The resulting PCR product was further subcloned into the RTM vector.

For RTM optimization, start codons and potential cryptic splice sites upstream of the splicing domain were modified with the QuikChange Lightning site-directed mutagenesis kit (Stratagene) resulting in three different RTMs: RTMorg, RTMm1, RTMm2. The sequence of each construct is provided in supplementary data 1.

Positive control: As positive control served a plasmid, expressing the fusion protein of SLCO1B3 and the HSV-TK (SLCO1B3-TK fusion) representing the accurate trans-splicing product between the TK-RTM and the SLCO1B3-MG. Herein the exon 3 of SLCO1B3 was amplified from SCLO1B3-MG using the Pfu turbo polymerase and the following primers (fw: 5'-gagagaattcatggaccaacatcaacattt-3', SEQ ID NO. 13; rv: 5'-ctagctgcagcttgaatccattgcagcgtc-3', SEQ ID NO. 14). The PCR product was further cloned into the TK-RTM-vector using EcoRI and PstI restriction sites, thereby removing the binding and splicing domain of the TK-RTM. Finally, the remaining PstI restriction site was removed from the CDS using the QuikChange Lightning site-directed mutagenesis kit (Stratagene).

Cell Culture and Transfection

For all screening experiments the human embryonic kidney cell line HEK293AD (Stratagene) was used. HEK293AD cells were grown in DMEM supplemented with 10% FCS and 100 U/ml penicillin/streptomycin (Biochrom) at 37° C. and 5% CO2 in a humidified incubator. The cells were passaged every 4 days by Trypsin-EDTA (Biochrom) treatment following centrifugation at 250 g for 5 min. Afterwards the cells were seeded in new tissue culture plates at desired density to reach 60% confluency the next day for plasmid transfection. Cells were transfected using the jetPEI reagent (Polyplus-transfection SA, Illkirch, France) according to the manufacturer's protocol.

RNA Isolation and cDNA Synthesis

Treated HEK293AD cells were considered for RNA isolation two days post transfection using the RNeasy Mini Kit (Qiagen) according to the manufacturer's protocol. 1 µg of purified RNA was DNase I digested for 30' at RT followed by cDNA synthesis using the iScriptTMcDNA Synthesis Kit (Biorad). For cDNA synthesis a mixture of oligo(dT) and random hexamer primers was provided.

SqRT-PCR

SqRT-PCR was performed to detect SLCO1B3-TK fusion transcripts in SLCO1B3-MG and TK-RTM co-transfected HEK293AD cells. For PCR analysis a SLCO1B3 specific forward primer (5'-ggaccaacatcaacatttgaataaaacagcagag-3' SEQ ID NO. 15), a HSV-TK specific reverse primer (5'-gtaagtcatcggctcgggta-3' SEQ ID NO. 16), cDNA of treated HEK293AD cells and GoTaq®qPCR Master Mix (Promega) were included. The PCR was performed under the following conditions with a Biorad CFX96TM system: 95° C. for 2 min, 40 cycles of 20 sec at 95° C., 20 sec at 64° C. and 20 sec at 72° C. The experiment was carried out in duplicates and repeated two times. Correct PCR products were verified by direct sequencing.

Western Blot Analysis

For immunostaining of the SLCO1B3-TK fusion protein HEK293AD cells were resuspended in RIPA lysis buffer (Santa Cruz) and extracted proteins were separated on a NuPAGE 4-12% BisTris gel (1.0 mm×12 well, Invitrogen) under denaturating conditions for 2 hours at 120 Volt. After equilibration of the SDS-gel in standard blotting buffer for up to 30 min at RT the proteins were electro-blotted onto a nitrocellulose membrane (Amersham Hybon-ECL, GE Healthcare) for 75 min at 0.25 Ampere. Subsequently, the membrane was soaked in blocking buffer (5% milk powder in TBS-T) for 1 hour at RT and incubated over night at 4° C. with first antibodies: goat anti-HSV-TK1 IgG (diluted 1:1000 in TBS-T) (Santa Cruz Biotechnology) and rabbit anti α-actinin IgG (diluted 1:000-1:5000 in TBS-T) (Santa Cruz Biotechnology). After three washings steps with TBS-T, the membrane was incubated with the secondary antibodies polyclonal rabbit anti-goat HRP (diluted 1:1000 in TBS-T, Dako) and HRP labelled Envision+ anti-rabbit antibody (diluted 1:500 in TBS-T, Dako), respectively. The blot was washed three times and visualization of specific protein bands was performed using the Immun-Star WesternC Kit (Biorad) and a ChemiDoc XRS Imager (Biorad).

Cell Viability Assay

The cell viability after RTM treatment was assessed by MTT (3-(4,5-Dimethylthiazol-2-yl)-2,5-diphenyltetrazolium bromide) assay (Sigma). 48 h after RTM transfection, HEK296AD cells were seeded into a 96 well plate (10,000 cells/well) and treated with 100 µM GCV (Cymevene®, Roche) the day after for 72 hours. 20 µl of MTT (5 g/L in PBS) were added to each well (200 µl) and incubated for approximately 2 hours at 37° C. Then, all media was removed and cells were lysed with 100 µl DMSO/Glycin (6 Vol DMSO+1 Vol 0.1M Glycin/NaOH pH10.2). After 10 min incubation on a plate shaker (500 rpm) the absorbance of the resultant formazan product was measured at 492 nm/620 nm with a plate photometer (Tecan). The percentage of cell viability was calculated by the equation: (OD GCV-treated/OD GCV-untreated)×100/negative control (OD GCV-treated/OD GCV-untreated). HEK293AD cells solely transfected with the SLCO1B3-MG served as negative control in this assay.

Terminal Deoxynucleotidyl Transferase dUTP Nick End Labeling (TUNEL) Assay

The detection of apoptosis was performed using the In Situ Cell Death Detection Kit, TMR red (Roche) according to the manufacture's protocol. Briefly, cells were washed with 1×PBS, fixed with 2% paraformaldehyde for 60 min at RT and permeabilized with 0.1% BSA/0.2% Triton X-100 in PBS for 5-10 min on ice. After 3 washing steps cells were incubated with TUNEL reaction solution for 1h at 37° C. in the dark and finally analyzed by fluorescence microscopy (Axiophot, Carl Zeiss) and flow cytometry (FC500, Beckman Coulter).

SEQUENCE LISTING

<160> NUMBER OF SEQ ID NOS: 23

<210> SEQ ID NO 1
<211> LENGTH: 1152
<212> TYPE: DNA
<213> ORGANISM: artificial
<220> FEATURE:
<223> OTHER INFORMATION: RTMorg

<400> SEQUENCE: 1

| | | | | | |
|---|---|---|---|---|---|
| gggtaagsgg | caagggtcga | acagagrgcg | cacgaggagc | tcaggggaaa cgctggtatc | 60 |
| ttatagttct | gtccgggttt | cgcactctga | cttgagcgtc | gattttgtga tgctcgtcag | 120 |
| gggrgcggag | cctatggaaa | aacgccagca | acgcggcctt | ttacggttcc tggcctttgc | 180 |
| tggccttttg | ctcacatgtt | ctttctgcgt | tatcccctga | ttctgtggat aaccgtatta | 240 |
| ccgccatgca | ttagttatta | atagtaatca | attacggggt | cattagttca tagcccatat | 300 |
| atggagttcc | gcgttacata | acttacggta | aatggcccgc | ctggctgacc gcccaacgac | 360 |
| ccccgcccat | tgacgtcaat | aatgacgtat | gttcccatag | taacgccaat agggactttc | 420 |
| cattgacgtc | aatgggtgga | gtatttacgg | taaactgccc | acttggcagt acatcaagtg | 480 |
| tatcatatgc | caagtacgcc | ccctattgac | gtcaatgacg | ctaaatggcc cgcctggcat | 540 |
| tatgcccagt | acatgacctt | atgggacttt | cctacttggc | agtacatcta cgtattagtc | 600 |
| atcgctatta | ccatggtgat | gcggttttgg | cagtacatca | atgggcgtgg atagcggttt | 660 |
| gactcacggg | gatttccaag | tctccacccc | attgacgtca | atgggagttt gttttggcac | 720 |
| caaaatcaac | gggactttcc | aaaatgtcgt | aacaactccg | ccccattgac gcaaatgggc | 780 |
| ggtaggcgtg | tacggtggga | ggtctatata | agcagagctg | gtttagtgaa ccgtcagatc | 840 |
| cgctagcgct | accggactca | gatctcgagc | tcaagcttcg | aattcatcga tgttagaaat | 900 |
| gcaaatcaat | actacaatga | gatgctatct | caccccccagt | taaatggct tatatcccaa | 960 |
| agacaggcaa | taacaaatgc | tggtgaggtt | gtggagtaaa | aacgagaaca ttattatagc | 1020 |
| gttgctcgag | tactaactgg | tacctcttct | tttttttctg | cagcccacgc tactgcgggt | 1080 |
| ttatatagac | ggtccccacg | ggatggggaa | aaccaccacc | acgcaactgc tggtggccyt | 1140 |
| ggtcsgsgsr | ra | | | | 1152 |

<210> SEQ ID NO 2
<211> LENGTH: 1196
<212> TYPE: DNA
<213> ORGANISM: artificial
<220> FEATURE:
<223> OTHER INFORMATION: RTMm1

<400> SEQUENCE: 2

| | | | | | |
|---|---|---|---|---|---|
| tcgraaacym | atgagaagag | kcgccaacga | gagggagctt | ccaaggggaa acgcctggwa | 60 |
| tcttatagtc | gtgtcagaga | tttggcmact | tctgacctga | aggmktcgat tttytgtgat | 120 |
| gctcgtcaag | gaggrgcgga | agcctatgaa | aaaacgccca | gcaacgcggc ttttacggt | 180 |
| ttcckggcct | tttgctggcc | ttttgctcac | awggttcttt | cctgcgttat ccctgattc | 240 |
| tgtggataac | cgtattaccg | ccatgcatta | gttattaata | gtaatcaatt acggggtcat | 300 |
| tagttcatag | cccatatatg | gagttccgcg | ttacataact | tacggtaaat ggcgcctgg | 360 |
| ctgacccgcc | caacgacccc | cgcccattga | cgtcaataat | gacgtatgtt cccatagtaa | 420 |
| cgccaatagg | gactttccat | tgacgtcaat | gggtggagta | tttacggtaa actgcccact | 480 |
| tggcagtaca | tcaagtgtat | catatgccaa | gtacgccccc | tattgacgtc aatgacgcta | 540 |

| | | |
|---|---|---|
| aatggcccgc ctggcattat gcccagtaca tgaccttatg ggactttcct acttggcagt | 600 |
| acatctacgt attagtcatc gctattacca tggtgatgcg gttttggcag tacatcaatg | 660 |
| ggcgtggata gcggtttgac tcacggggat ttccaagtct ccaccccatt gacgtcaatg | 720 |
| ggagtttgtt ttggcaccaa aatcaacggg actttccaaa atgtcgtaac aactccgccc | 780 |
| cattgacgca aatgggcggt aggcgtgtac ggtgggaggt ctatataagc agagctggtt | 840 |
| tagtgaaccg tcagatccgc tagcgctacc ggactcagat ctcgagctca agcttcgaat | 900 |
| tcatcgattt tagaaatcca atcaatact acaattagat cctatctcac ccccagttaa | 960 |
| aatcgcttat atcccaaaga caggcaataa caaatcctgg gggggttgt ggagcaaaaa | 1020 |
| cgaggaattc gttaacgata tcgagaacat tattatagcg ttgctcgagt actaactggt | 1080 |
| acctcttctt tttttctgc agcccacgct actgcgggtt tatatagacg gtccccacgg | 1140 |
| gatggggaaa accaccacca cgcaactgct ggtkgcccct ggttsgcssm rcmrrt | 1196 |

<210> SEQ ID NO 3
<211> LENGTH: 1186
<212> TYPE: DNA
<213> ORGANISM: artificial
<220> FEATURE:
<223> OTHER INFORMATION: RTMm2

<400> SEQUENCE: 3

| | | |
|---|---|---|
| acgagmtrgg ttcsgaatma gagrargsgc aacgaaggag cttcagggaa cgcctggwtc | 60 |
| ttatagtccc tgtccgrgtt cgccacctcc tgacttgaag cgtcgatttt tgtgatgstc | 120 |
| gtcaagrggr gscggaagcc tatggaaaaa acgcagcaac gcggccttt ttacggttcc | 180 |
| tggcctttks tggcctttgc tcacatgttc tttctgcgtt atccctgatt ctgkggataa | 240 |
| ccgtattacc gccatgcatt agttattaat agtaatcaat tacggggtca ttagttcata | 300 |
| gcccatata tggagttccg cgttacataa cttacggtaa atggcccgcc tggctgaccg | 360 |
| cccaacgacc cccgcccatt gacgtcaata atgacgtatg ttcccatagt aacgccaata | 420 |
| gggactttcc attgacgtca atgggtggag tatttacggt aaactgccca cttggcagta | 480 |
| catcaagtgt atcatatgcc aagaacgccc cctattgacg caatgacgg aaaatggccc | 540 |
| gcctggcatt atcccagta catcaccta tcggactttc ctacttggca gtacatctac | 600 |
| gtattagtca tcgctattac catggtgatg cggttttggc agtacatcaa tgggcgtgga | 660 |
| tagcggtttg actcacgggg atttccaagt ctccaccca ttgacgtcaa tgggagtttg | 720 |
| ttttggcacc aaaatcaacg ggactctcca aatttcgta acaactccgc cccattgacg | 780 |
| caaatcggcg gtaggcgtgt acggtgggag gtctatataa gcagagctgg tttagttaac | 840 |
| cgtcagatcc gctagcgcta ccggactcag atctcgagct caagcttcga attcatcgat | 900 |
| tttagaaatc caaatcaata ctacaattag atcctatctc accccagtt aaaatcgctt | 960 |
| atatcccaaa acaggcaat aacaaatcct gggggggtt gtggagcaaa aacgaggaat | 1020 |
| tcgttaacga tatcgagaac attattatag cgttgctcga gtactaactg gtacctcttc | 1080 |
| tttttttct gcagcccacg ctactgcggg tttatataga cggtccccac gggatgggga | 1140 |
| aaaccaccac cacgcaactg ctggtggcct ggtcgcgmsr amysag | 1186 |

<210> SEQ ID NO 4
<211> LENGTH: 107
<212> TYPE: DNA
<213> ORGANISM: artificial
<220> FEATURE:

<223> OTHER INFORMATION: RTMorg BD

<400> SEQUENCE: 4
agaaatgcaa atcaatacta caatgagatg ctatctcacc cccagttaaa atggcttata    60
tcccaaagac aggcaataac aaatgctggt gaggttgtgg agtaaaa    107

<210> SEQ ID NO 5
<211> LENGTH: 108
<212> TYPE: DNA
<213> ORGANISM: artificial
<220> FEATURE:
<223> OTHER INFORMATION: RTMm1 BD

<400> SEQUENCE: 5
agaaatccaa atcaatacta caattagatc ctatctcacc cccagttaaa atcgcttata    60
tcccaaagac aggcaataac aaatcctggg gggggttgtg gagcaaaa    108

<210> SEQ ID NO 6
<211> LENGTH: 108
<212> TYPE: DNA
<213> ORGANISM: artificial
<220> FEATURE:
<223> OTHER INFORMATION: RTMm2 BD

<400> SEQUENCE: 6
agaaatccaa atcaatacta caattagatc ctatctcacc cccagttaaa atcgcttata    60
tcccaaagac aggcaataac aaatcctggg ggggttgtg gagcaaaa    108

<210> SEQ ID NO 7
<211> LENGTH: 58
<212> TYPE: DNA
<213> ORGANISM: artificial
<220> FEATURE:
<223> OTHER INFORMATION: primer

<400> SEQUENCE: 7
gatcgatatc gaatgggttt tatattttca aactaaaata agttaatgga aaattttt    58

<210> SEQ ID NO 8
<211> LENGTH: 53
<212> TYPE: DNA
<213> ORGANISM: artificial
<220> FEATURE:
<223> OTHER INFORMATION: primer

<400> SEQUENCE: 8
gagagcggcc gcgatttgaa tatacatttc tcaaagaag acatacaaat agc    53

<210> SEQ ID NO 9
<211> LENGTH: 42
<212> TYPE: DNA
<213> ORGANISM: artificial
<220> FEATURE:
<223> OTHER INFORMATION: primer

<400> SEQUENCE: 9
gatcaagctt atggaccaac atcaacattt gaataaaaca gc    42

<210> SEQ ID NO 10
<211> LENGTH: 53
<212> TYPE: DNA
<213> ORGANISM: artificial
<220> FEATURE:
<223> OTHER INFORMATION: primer

<400> SEQUENCE: 10
gagagcggcc gcgatttgaa tatacatttc tcaaaagaag acatacaaat agc        53

<210> SEQ ID NO 11
<211> LENGTH: 30
<212> TYPE: DNA
<213> ORGANISM: artificial
<220> FEATURE:
<223> OTHER INFORMATION: primer

<400> SEQUENCE: 11
ctagctgcag cccacgctac tgcgggttta                                  30

<210> SEQ ID NO 12
<211> LENGTH: 33
<212> TYPE: DNA
<213> ORGANISM: artificial
<220> FEATURE:
<223> OTHER INFORMATION: primer

<400> SEQUENCE: 12
gagagaggat cctcagttag cctcccccat ctc                              33

<210> SEQ ID NO 13
<211> LENGTH: 30
<212> TYPE: DNA
<213> ORGANISM: artificial
<220> FEATURE:
<223> OTHER INFORMATION: primer

<400> SEQUENCE: 13
gagagaattc atggaccaac atcaacattt                                  30

<210> SEQ ID NO 14
<211> LENGTH: 30
<212> TYPE: DNA
<213> ORGANISM: artificial
<220> FEATURE:
<223> OTHER INFORMATION: primer

<400> SEQUENCE: 14
ctagctgcag cttgaatcca ttgcagcgtc                                  30

<210> SEQ ID NO 15
<211> LENGTH: 34
<212> TYPE: DNA
<213> ORGANISM: artificial
<220> FEATURE:
<223> OTHER INFORMATION: primer

<400> SEQUENCE: 15
ggaccaacat caacatttga ataaaacagc agag                             34

<210> SEQ ID NO 16
<211> LENGTH: 20
<212> TYPE: DNA
<213> ORGANISM: artificial
<220> FEATURE:
<223> OTHER INFORMATION: primer

<400> SEQUENCE: 16
gtaagtcatc ggctcgggta                                             20

<210> SEQ ID NO 17

<211> LENGTH: 290
<212> TYPE: DNA
<213> ORGANISM: artificial
<220> FEATURE:
<223> OTHER INFORMATION: Intron 3 of SLCO1B3

<400> SEQUENCE: 17

```
cacgtggtag ctcaattttt agttccttga ggaacctcca gactgttctt catagtggtc    60
ctactaattt ttattgctac caacagtgta caaggaattc cttttactcc acaacctcac   120
cagcatttgt tattgcctgt ctttgggata taagccattt taactggggg tgagatagca   180
tctcattgta gtattgattt gcatttctct gatgatcact gatgttgagc acttcttcct   240
atgcctgtgt gctatttgta tgtcttcttt tgagaaatgt atattcaaat              290
```

<210> SEQ ID NO 18
<211> LENGTH: 107
<212> TYPE: DNA
<213> ORGANISM: artificial
<220> FEATURE:
<223> OTHER INFORMATION: BD within intron 3 of SLCO1B3

<400> SEQUENCE: 18

```
ttttactcca caacctcacc agcatttgtt attgcctgtc tttgggatat aagccatttt    60
aactggggt gagatagcat ctcattgtag tattgatttg catttct                  107
```

<210> SEQ ID NO 19
<211> LENGTH: 107
<212> TYPE: DNA
<213> ORGANISM: artificial
<220> FEATURE:
<223> OTHER INFORMATION: Consensus sequence for alignment of intron 3
     and BD

<400> SEQUENCE: 19

```
ttttactcca caacctcacc agcatttgtt attgcctgtc tttgggatat aagccatttt    60
aactggggt gagatagcat ctcattgtag tattgatttg catttct                  107
```

<210> SEQ ID NO 20
<211> LENGTH: 580
<212> TYPE: DNA
<213> ORGANISM: artificial
<220> FEATURE:
<223> OTHER INFORMATION: RTMorg

<400> SEQUENCE: 20

```
catatgccaa gtacgccccc tattgacgtc aatgacgcta atggcccgc ctggcattat    60
gcccagtaca tgaccttatg gactttcct acttggcagt acatctacgt attagtcatc   120
gctattacca tggtgatgcg gttttggcag tacatcaatg ggcgtggata gcggtttgac   180
tcacggggat ttccaagtct ccaccccatt gacgtcaatg ggagtttgtt ttggcaccaa   240
aatcaacggg actttccaaa atgtcgtaac aactccgccc cattgacgca aatgggcggt   300
aggcgtgtac ggtgggaggt ctatataagc agagctggtt tagtgaaccg tcagatccgc   360
tagcgctacc ggactcagat ctcgagctca agcttcgaat tcatcgatgt tagaaatgca   420
aatcaatact acaatgagat gctatctcac ccccagttaa aatggcttat atcccaagaa   480
caggcaataa caaatgctgg tgaggttgtg gagtaaaaac gagaacatta ttatagcgtt   540
gctcgagtac taactggtac ctcttctttt ttttctgcag                        580
```

<210> SEQ ID NO 21

```
<211> LENGTH: 602
<212> TYPE: DNA
<213> ORGANISM: artificial
<220> FEATURE:
<223> OTHER INFORMATION: RTMm1

<400> SEQUENCE: 21
catatgccaa gtacgccccc tattgacgtc aatgacgcta aatggcccgc ctggcattat      60
gcccagtaca tgaccttatg ggactttcct acttggcagt acatctacgt attagtcatc    120
gctattacca tggtgatgcg gttttggcag tacatcaatg ggcgtggata gcggtttgac    180
tcacggggat ttccaagtct ccaccccatt gacgtcaatg ggagtttgtt ttggcaccaa    240
aatcaacggg actttccaaa atgtcgtaac aactccgccc cattgacgca aatgggcggt    300
aggcgtgtac ggtgggaggt ctatataagc agagctggtt tagtgaaccg tcagatccgc    360
tagcgctacc ggactcagat ctcgagctca agcttcgaat tcatcgattt tagaaatcca    420
aatcaatact acaattagat cctatctcac ccccagttaa aatcgcttat atcccaaaga    480
caggcaataa caaatcctgg gggggttgt ggagcaaaaa cgaggaattc gttaacgata    540
tcgagaacat tattatagcg ttgctcgagt actaactggt acctcttctt tttttctgc     600
ag                                                                    602

<210> SEQ ID NO 22
<211> LENGTH: 602
<212> TYPE: DNA
<213> ORGANISM: artificial
<220> FEATURE:
<223> OTHER INFORMATION: RTMm2

<400> SEQUENCE: 22
catatgccaa gaacgccccc tattgacgac aatgacggaa aatggcccgc ctggcattat      60
ccccagtaca tcaccttatc ggactttcct acttggcagt acatctacgt attagtcatc    120
gctattacca tggtgatgcg gttttggcag tacatcaatg ggcgtggata gcggtttgac    180
tcacggggat ttccaagtct ccaccccatt gacgtcaatg ggagtttgtt ttggcaccaa    240
aatcaacggg actctccaaa atttcgtaac aactccgccc cattgacgca aatcggcggt    300
aggcgtgtac ggtgggaggt ctatataagc agagctggtt tagttaaccg tcagatccgc    360
tagcgctacc ggactcagat ctcgagctca agcttcgaat tcatcgattt tagaaatcca    420
aatcaatact acaattagat cctatctcac ccccagttaa aatcgcttat atcccaaaga    480
caggcaataa caaatcctgg gggggttgt ggagcaaaaa cgaggaattc gttaacgata    540
tcgagaacat tattatagcg ttgctcgagt actaactggt acctcttctt tttttctgc     600
ag                                                                    602

<210> SEQ ID NO 23
<211> LENGTH: 602
<212> TYPE: DNA
<213> ORGANISM: artificial
<220> FEATURE:
<223> OTHER INFORMATION: Consensus sequence for alignment of RTMorg,
      RTMm1, RTMm2

<400> SEQUENCE: 23
catatgccaa gtacgcccccc tattgacgtc aatgacgcta aatggcccgc ctggcattat     60
gcccagtaca tgaccttatg ggactttcct acttggcagt acatctacgt attagtcatc    120
gctattacca tggtgatgcg gttttggcag tacatcaatg ggcgtggata gcggtttgac    180
```

-continued

| | | | | |
|---|---|---|---|---|
| tcacggggat | ttccaagtct | ccaccccatt | gacgtcaatg | ggagtttgtt | ttggcaccaa | 240 |
| aatcaacggg | actttccaaa | atgtcgtaac | aactccgccc | cattgacgca | aatgggcggt | 300 |
| aggcgtgtac | ggtgggaggt | ctatataagc | agagctggtt | tagtgaaccg | tcagatccgc | 360 |
| tagcgctacc | ggactcagat | ctcgagctca | agcttcgaat | tcatcgattt | tagaaatcca | 420 |
| aatcaatact | acaattagat | cctatctcac | ccccagttaa | aatcgcttat | atcccaaaga | 480 |
| caggcaataa | caaatcctgg | gggggttgt | ggagcaaaaa | cgaggaattc | gttaacgata | 540 |
| tcgagaacat | tattatagcg | ttgctcgagt | actaactggt | acctcttctt | tttttctgc | 600 |
| ag | | | | | | 602 |

The invention claimed is:

1. A method for treating a disease, wherein said method comprises administering, to a subject in need of such treatment, an RNA trans-splicing molecule (RTM) comprising a splicing domain, a coding domain, and a binding domain, characterized in that
   (a) the splicing domain comprises a strong conserved branch point (BP) sequence, a polypyrimidine (PPT), and a 3' acceptor splice site (ss);
   (b) the coding domain comprises a suicide gene sequence thymidine kinase from herpes simplex virus (HSV-tk), and
   (c) the binding domain comprises a sequence complementary to intron 3 of the pre-mRNA of solute carrier organic anion transporter family member 1B3 (SLCO1B3).

2. The method, according to claim 1, wherein said disease is a proliferative disease.

3. The method, according to claim 2, wherein said proliferative disease is selected from squamous cell carcinoma, epidermolysis bullosa, cystic fibrosis, pachyonychia congenita, psoriasis and neurodermitis.

* * * * *

UNITED STATES PATENT AND TRADEMARK OFFICE
CERTIFICATE OF CORRECTION

PATENT NO. : 9,655,979 B2
APPLICATION NO. : 14/438625
DATED : May 23, 2017
INVENTOR(S) : Johann Bauer et al.

Page 1 of 1

It is certified that error appears in the above-identified patent and that said Letters Patent is hereby corrected as shown below:

In the Specification

Column 7,
Line 60, "Man P" should read -- Marr P --.

Column 16,
Line 24, "3.1DN5-His-TOPO" should read -- 3.1D/V5-His-TOPO --.
Line 63, "rv: 540" should read -- rv: 5' --.

Signed and Sealed this
Twenty-third Day of January, 2018

Joseph Matal
*Performing the Functions and Duties of the
Under Secretary of Commerce for Intellectual Property and
Director of the United States Patent and Trademark Office*